(12) United States Patent
Lerchl et al.

(10) Patent No.: US 7,179,647 B2
(45) Date of Patent: Feb. 20, 2007

(54) ELONGASE GENE AND METHOD FOR PRODUCING POLYUNSATURATED FATTY ACIDS

(75) Inventors: Jens Lerchl, Svalöv (SE); Ernst Heinz, Hamburg (DE); Thorsten Zank, Hamburg (DE)

(73) Assignee: BASF Plant Science GmbH (DE)

( * ) Notice: Subject to any disclaimer, the term of this patent is extended or adjusted under 35 U.S.C. 154(b) by 0 days.

(21) Appl. No.: 10/502,083

(22) PCT Filed: Jan. 13, 2003

(86) PCT No.: PCT/EP03/00221

§ 371 (c)(1),
(2), (4) Date: Jul. 22, 2004

(87) PCT Pub. No.: WO03/064638

PCT Pub. Date: Aug. 7, 2003

(65) Prior Publication Data

US 2005/0214761 A1 Sep. 29, 2005

(30) Foreign Application Priority Data

Jan. 30, 2002 (DE) ............... 102 03 713
Feb. 11, 2002 (DE) ............... 102 05 607

(51) Int. Cl.
| | | |
|---|---|---|
| C12N 5/00 | (2006.01) | |
| C12N 9/02 | (2006.01) | |
| C12N 9/88 | (2006.01) | |
| C12P 7/64 | (2006.01) | |
| C07H 21/04 | (2006.01) | |
| C12N 15/00 | (2006.01) | |
| C12N 1/20 | (2006.01) | |

(52) U.S. Cl. ............... 435/325; 435/134; 435/410; 435/69.1; 435/193; 435/252.3; 435/320.1; 536/23.2

(58) Field of Classification Search ............ 435/183, 435/69.1; 800/295
See application file for complete search history.

(56) References Cited

U.S. PATENT DOCUMENTS

| | | | |
|---|---|---|---|
| 5,475,099 A | 12/1995 | Knauf et al. | |
| 5,614,393 A | 3/1997 | Thomas et al. | |
| 6,913,916 B1 * | 7/2005 | Mukerji et al. | 435/183 |
| 2005/0089981 A1 * | 4/2005 | Napier et al. | 435/193 |

FOREIGN PATENT DOCUMENTS

| | | |
|---|---|---|
| EP | 0 550 162 A1 | 7/1993 |
| EP | 0 794 250 A1 | 9/1997 |
| WO | WO 91/13972 | 9/1991 |
| WO | WO 93/06712 | 4/1993 |
| WO | WO 93/11245 | 6/1993 |
| WO | WO 94/11516 | 5/1994 |
| WO | WO 94/18337 | 8/1994 |
| WO | WO 95/15387 | 6/1995 |
| WO | WO 95/18222 | 7/1995 |
| WO | WO 96/13582 | 5/1996 |
| WO | WO 96/21022 | 7/1996 |
| WO | WO 97/21340 | 6/1997 |
| WO | WO 97/30582 | 8/1997 |
| WO | WO 98/46763 | 10/1998 |
| WO | WO 98/46764 | 10/1998 |
| WO | WO 98/46765 | 10/1998 |
| WO | WO 98/46776 | 10/1998 |
| WO | WO 98/54954 | 12/1998 |
| WO | WO 99/27111 | 6/1999 |
| WO | WO 99/64616 | 12/1999 |

OTHER PUBLICATIONS

Wallis et al. trend in biochem Sci., 2002, vol. 27, pp. 467-473.*
Abbadi, Amine et al., "Transgenic Oilseeds as Sustainable Source of Nutritionally Relevant C20 and C22 Polyunsaturated Fatty Acids?," *Eur. J. Lipid Sci. Technol*, 103:106-113 (2001).
Certik, Milan et al., "Desaturase-Defective Fungal Mutants: Useful Tools for the Regulation and overproduction of Polyunsaturated Fatty Acids," *Trends in Biotechnology*, 16:500-505 (1998).
Cronan, John E., Jr. et al., "Biosynthesis of Membrane Lipids," *E. coli und Salmonella*, AMS Press, Washington, DC; pp. 612-636 (1996).
Frentzen, Margrit, "Acyltransferases from Basic Science to Modified Seed Oils," *Lipid*, 100(4-5):161-166 (1998).
Gernardt, Bernt, Fatty Acid Degradation in Plants, *Progress in Lipid Research*, 31(4):417-446 (1992).
Gühmemann-Schäfer, Kerstin et al., "Fatty Acid β-Oxidation in Glyoxysomes. Characterization of a New Tetrafunctional Protein (MFP III)," *Biochimica et Biophysica Acta*, 1256:181-186 (1995).

(Continued)

Primary Examiner—Rebecca E. Prouty
Assistant Examiner—Mohammad Meah
(74) *Attorney, Agent, or Firm*—Connolly Bove Lodge & Hutz LLP

(57) ABSTRACT

The invention relates to a novel elongase gene with the sequence SEQ ID NO: 1 or its homologs, derivatives or analogs, to a gene construct comprising this gene or its homologs, derivatives and analogs, and to its use. The invention also relates to vectors or organisms comprising an elongase gene with the sequence SEQ ID No: 1 or its homologs, derivatives or analogs. Furthermore, the invention relates to a process for the preparation of polyunsaturated fatty acids and to a process for introducing DNA into organisms which produce large amounts of oils and, in particular, oils with a high content of unsaturated fatty acids. Moreover, the invention relates to an oil and/or a fatty acid preparation with a higher content of polyunsaturated fatty acids with at least two double bonds and/or a triacyiglycerol preparation with a higher content of polyunsaturated fatty acids with at least two double bonds.

13 Claims, No Drawings

OTHER PUBLICATIONS

Huang, Yung-Sheng et al., "Cloning of Δ12- and Δ6-Desaturates from *Mortierella alpina* and Recombinant Production of γ-Linolenic Acid in *Saccharomyces cerevisiae*," *Lipids*, 34(7):649-659 (1999).

Kinney, Anthony J., "Genetic Engineering of Oilseeds for Desired Traits," *Genetic Engineering*, 19:149-166 (1997).

Kunau, Wolf-H et al., "β-Oxidation of Fatty Acids in Mitochondria, Peroxisomes, and Bacteria: A Century of Continued Progress," *Progress in Lipid Research*, 34(4):267-342 (1995).

Magnuson, Kelly et al., "Regulation of Fatty Acid Biosynthesis in *Escherichia coli*," *Microbiological Reviews*, 57(3):522-542 (1993).

Murphy, Denis J. et al., "Biosynthesis, Targeting and Processing of Olesin-Like Proteins, which are Major Pollen Coat Components in *Brassica napus*," *The Plant Journal*, 13(1):1-16 (1998).

Napier, Johnathan A. et al., "Identification of a *Caenorhabditis elegans* Δ6-Fatty-Acid-Desaturase by Heterologous Expression in *Saccharomyces cerevisiae*," *Biochemical Journal*, 330:611-614 (1998).

Ohlrogge, John et al., "Lipid Biosynthesis," *The Plant Cell*, 7:957-970 (1995).

Shanklin, John et al., "Desaturation and Related Modifications of Fatty Acids," *Annual Review of Plant Physiology and Plant Molecular Biology*, 49:611-641 (1998).

Simopoulos, Artemis, P., "Essential Fatty Acids in Health and Chronic Disease," *The American Journal of Clinical Nutrition*, 70(supp):560S-569S (1999).

Stukey, Joseph E. et al., "The *OLE1* Gene *Sacchaeomyces cerevisiae* Encodes the Δ9 Fatty Acid Desaturase and Can be Functionally Replaced by the Rat Stearoyl-CoA Desaturase Gene," *The Journal of Biological Chemistry*, 265(33):20144-20149 (1990).

Stymme, Sten, "Biosynthesis of 'Uncommon' Fatty Acids and Their Incorporation into Triacylglycerols," *Biochemistry and Molecular Biology of Membrane and Storage Lipids of Plants*, N. Murata and Somerville eds., American Society of Plant Physiologists, pp. 150-158 (1993).

Takahata, Kyoya et al., "The Benefits and Risks of n-3 Polyunsaturated Fatty Acids," *Bioscience, Biotechnology, and Biochemistry*, 62(11):2079-2085 (1998).

Voelker, Toni, "Plant Acyl-ACP Thioesterases: Chain-Length Determining Enzymes in Plant Fatty Acid Biosynthesis," *Genetic Engineering*, 18:111-113 (1996).

Wada, Hajime et al., "Enhancement of Chilling Tolerance of a Cyanobacterium by Genetic Manipulation of Fatty Acid Desaturation," *Nature*, 347:200-203 (1990).

Wang, Xuemin M. et al., "Biosynthesis and Regulation of Linolenic Acid in Higher Plants," *Plant Physiology and Biochemistry*, 26(6):777-792 (1988).

DATABASE Accession No. DC257414, May 24, 2003.

DATABASE Accession No. BE775687, May 29, 2003.

Kamoun, Sophien, et al., "Initial Assessment of Gene Diversity for the Oomycete Pathogen *Phytophthora infestans* Based on Expressed Sequences," *Fungal Genetics and Biology*, 28:94-107 (1999).

Willich, S.N., et al., "Omega-3 Fatty Acids (Fish Oil) in their Clinical Application," *Deutsche Medizinische Wochenschrift*, 120(7):227-233 (1995). Note: No English Abstract Available.

* cited by examiner

ELONGASE GENE AND METHOD FOR PRODUCING POLYUNSATURATED FATTY ACIDS

RELATED APPLICATIONS

This application is a national stage application (under 35 U.S.C. 371) of PCT/EP03/00221 filed Jan. 13, 2003, which claims benefit of German application 102 03 713.2 filed Jan. 30, 2002, and German application 102 05 607.2 filed Feb. 11, 2002.

FIELD OF THE INVENTION

The invention relates to a novel elongase gene with the sequence SEQ ID NO:1 or its homologs, derivatives or analogs, to a gene construct comprising this gene or its homologs, derivatives and analogs, and to its use. The invention also relates to vectors or organisms comprising an elongase gene with the sequence SEQ ID NO:1 or its homologs, derivatives or analogs.

DESCRIPTION OF THE BACKGROUND

Furthermore, the invention relates to a process for the preparation of polyunsaturated fatty acids and to a process for introducing DNA into organisms which produce large amounts of oils and, in particular, oils with a high content of unsaturated fatty acids. Moreover, the invention relates to an oil and/or a fatty acid preparation with a higher content of polyunsaturated fatty acids with at least two double bonds and/or a triacylglycerol preparation with a higher content of polyunsaturated fatty acids with at least two double bonds.

Certain products and byproducts of naturally occurring metabolic processes in microbial cells or in the cells of animals and, advantageously, plants can be used for a wide spectrum of industries, including the animal feed industry, food industry, cosmetics industry and pharmaceuticals industry. These molecules, which are jointly referred to as "fine chemicals", also include lipids and fatty acids, amongst which the polyunsaturated fatty acids constitute an example of one class. Polyunsaturated fatty acids (PUFAs) are added, for example, to food for children to increase the nutritional value of these foods. For example, PUFAs have a positive effect on the cholesterol level in the blood of humans and are therefore suitable for protection against heart disease. Fine chemicals such as polyunsaturated fatty acids (PUFAs) can be isolated from animal sources, for example fish or produced on a large scale using microorganisms by growing microorganisms which have been developed in such a way that they produce and accumulate or secrete, large amounts of one or more desired molecules.

Microorganisms which are especially suitable for preparing PUFAs are microorganisms such as algae such as *Phaeodactylum tricornutum* or *Crypthecodinium* species, Ciliata such as *Stylonychia* or *Colpidium*, fungi such as *Mortierella*, *Entomophthora* or *Mucor*. A number of mutant strains of the microorganisms in question which produce a series of desirable compounds, including PUFAs, have been developed by strain selection. The selection of strains with an improved production of a certain molecule is, however, a time-consuming and difficult procedure.

As an alternative, fine chemicals can suitably be produced on a large scale via the production of plants which have been developed in such a way that they produce the abovementioned PUFAs. Plants which are particularly well suited to this purpose are oil crops which contain large amounts of lipid compounds, such as oilseed rape, canola, linseed, soya, sunflowers, thistles, borage and evening primrose. However, other crops which contain oils or lipids and fatty acids are well suited, as mentioned in the detailed description of the present invention. Conventional plant breeding via the selection of suitable plants has led to the development of a series of mutant plants which produce a spectrum of desirable lipids and fatty acids, cofactors and enzymes. However, the selection of novel plant varieties with an improved production of a certain molecule is a time-consuming and difficult procedure or even impossible if the compound does not occur naturally in the plant in question, such as in the case of polyunsaturated $C_{20}$-fatty acids and those with longer carbon chains.

SUMMARY OF THE INVENTION

Owing to the positive characteristics of unsaturated fatty acids, there has been no lack of attempts in the past to make available genes which are involved in the synthesis of fatty acids or triglycerides for the production, in various organisms, of oils with a modified content of unsaturated fatty acids. Thus, WO 91/13972 and its US equivalent describe a Δ-9 desaturase. WO 93/11245 claims a Δ-15 desaturase, and WO 94/11516 a Δ-12 desaturase. Δ-6 desaturases are described in WO 93/06712, U.S. Pat. No. 5,614,393, WO 96/21022 and WO 99/27111. Further desaturases are described, for example, in EP-A-0 550 162, WO 94/18337, WO 97/30582, WO 97/21340, WO 95/18222, EP-A-0 794 250, Stukey et al., J. Biol. Chem., 265, 1990: 20144–20149, Wada et al., Nature 347, 1990: 200–203 or Huang et al., Lipids 34, 1999: 649–659. WO 96/13591 describes and claims a Δ-6-palmitoyl-ACP desaturase. However, the various desaturases have hitherto been insufficiently characterized in terms of their biochemistry since the enzymes, being membrane-bound proteins, can only be isolated and characterized with great difficulty (McKeon et al., Methods in Enzymol. 71, 1981: 12141–12147, Wang et al., Plant Physiol. Biochem., 26, 1988: 777–792).

Both a shift in the fatty acid spectrum towards unsaturated fatty acids and an increase in the productivity have been identified in yeasts (see Huang et al., Lipids 34, 1999: 649–659, Napier et al., Biochem. J., Vol. 330, 1998: 611–614). However, the expression of the various desaturases in transgenic plants was not as successful as desired. A shift of the fatty acid spectrum for unsaturated fatty acids has not been found, while it has been found at the same time that the synthesis productivity of the transgenic plants was greatly reduced, i.e. only small amounts of oils in comparison with the starting plants were isolated.

The cloning and expression of elongases which elongate unsaturated fatty acids as substrate of the enzyme reaction by at least two C atoms has hitherto been described neither for yeasts nor for plants.

This means that neither yeasts nor crop plants naturally produce polyunsaturated $C_{20}$- and/or $C_{22}$-fatty acids with at least two double bonds in the fatty acid molecule, such as arachidonic acid (ARA) and/or eicosapentaenoic acid (EPA) and/or docosahexaenoic acid (DHA).

A great need therefore still exists for novel genes which encode enzymes which are involved in the biosynthesis of unsaturated fatty acids and which make possible the production of the latter on an industrial scale. There is a particularly great need for elongases which elongate unsaturated fatty acids by at least two C atoms. None of the prior-art biotechnological methods for the production of polyunsaturated fatty acids yields the abovementioned fatty acids in economically utilizable quantities.

Again and again, the expression of genes in plants involves problems, that is to say that the expression does not provide the expected increase in the production of the desired product of value.

It was therefore an object to identify, clone and express novel elongase genes and thus to provide them for the synthesis of unsaturated fatty acids, such as polyunsaturated $C_{20}$- and/or $C_{22}$-fatty acids with at least two double bonds in the fatty acid molecule, such as arachidonic acid (ARA) and/or eicosapentaenoic acid (EPA) and/or docosahexaenoic acid (DHA).

This object was achieved by the isolated nucleic acid according to the invention, which encodes a polypeptide which elongates $C_{16}$- or $C_{18}$-fatty acids with at least two double bonds in the fatty acid by at least two carbon atoms, the fatty acids $C_{18:3}^{\Delta 5t,9,12}$, $C_{20:3}^{\Delta 8,11,14}$, $C_{20:4}^{\Delta 5,8,11,14}$ und $C_{20:5\Delta 5,8,11,14,17}$ not being elongated.

The object is achieved advantageously by an isolated nucleic acid comprising a nucleotide sequence which encodes a polypeptide which elongates $C_{16}$- or $C_{18}$-fatty acids with at least two double bonds in the fatty acid molecule, selected from the group consisting of
a) a nucleic acid sequence shown in SEQ ID NO:1,
b) a nucleic acid sequence which, in accordance with the degeneracy of the genetic code, is derived from the sequence shown in SEQ ID NO:2,
c) derivatives of the sequence shown in SEQ ID NO:1 which encode the polypeptides with at least 50% homology with the sequence encoding the amino acid sequences in SEQ ID NO:2, the sequence acting as $C_{16}$- or $C_{18}$-elongase.

Preferably, the nucleotide sequence selected from the above group elongates $C_{16}$- or $C_{18}$-fatty acids with at least two double bonds in the fatty acid by at least two carbon atoms, with the following fatty acids, however, not being elongated $C_{18:3}^{\Delta 5t,9,12}$, $C_{20:3}^{\Delta 8,11,14}$, $C_{20:4}^{\Delta 5,8,11,14}$ and $C_{20:5\Delta 5,8,11,14,17}$. $C_{16}$- or $C_{18}$-fatty acids with two, three or four double bonds in the fatty acid molecule are preferably elongated. While fatty acids such as $C_{18:3}^{\Delta 5t,9,12}$, $C_{20:3}^{\Delta 8,11,14}$, $C_{20:4}^{\Delta 5,8,11,14}$ and $C_{20:5}^{\Delta 5,8,11,14,17}$ are not elongated, fatty acids selected from the group consisting of $C_{18:2}^{\Delta 9,12}$, $C_{18:3}^{\Delta 4,7,10}$, $C_{18:3}^{\Delta 5,8,11}$, $C_{18:3}^{\Delta 6,9,12}$, $C_{18:3}^{\Delta 7,10,13}$, $C_{18:3}^{\Delta 8,11,14}$, $C_{18:3}^{\Delta 9,12,15}$, $C_{18:4}^{\Delta 6,9,12,15}$, $C_{18:3}^{\Delta 5c,9,12}$ or $C_{16:3}^{\Delta 7,10,13}$ are elongated. The elongases according to the invention show a preference for $C_{18:3}^{\Delta 6,9,12}$-, $C_{18:4}^{\Delta 6,9,12,15}$- and $C_{16:3}^{\Delta 7,10,13}$-fatty acids which exceeds that for unsaturated fatty acids such as $C_{18:2}^{\Delta 9,12}$-, $C_{18:3}^{\Delta 4,7,10}$-, $C_{18:3}^{\Delta 5,8,11}$-, $C_{18:3}^{\Delta 7,10,13}$-, $C_{18:3}^{\Delta 8,11,14}$-, $C_{18:3}^{\Delta 9,12,15}$- or $C_{18:3}^{\Delta 5,c9,12}$-fatty acids by advantageously at least a factor of 1.5, preferably at least by the factor 1.6, especially preferably at least by the factor 1.7, or very especially preferably by at least the factor 1.8.

The nucleic acid sequences according to the invention, which elongate $C_{16}$- or $C_{18}$-fatty acids, originally advantageously originate from fungi, preferably from fungi such as the Oomycetes, for example Oomycetes such as those of the genus *Phytophthora*, especially preferably from Oomycetes of the genus and species *Phytophthora infestans*.

The nucleic acids according to the invention can be used for the modification of oils, fatty acids, lipids, lipid-derived compounds and most preferably for the production of polyunsaturated fatty acids.

Host organisms which are advantageously suitable for the nucleic acids according to the invention are microorganisms such as *Phaeodactylum, Colpidium, Mortierella, Entomophthora, Mucor, Crypthecodinium* and other algae and fungi, and plants, in particular oil crops, which are used on a large scale in industry for the production of a multiplicity of fine chemicals.

Using the cloning vectors and techniques for the genetic manipulation of the abovementioned microorganisms and ciliates disclosed in, for example, WO 98/01572 or the methods and vectors described in Falciatore et al., 1999, Marine Biotechnology 1(3):239–251, and Dunahay et al., 1995, Genetic transformation of diatoms, J. Phycol. 31:10004–1012 and the references cited therein for algae and related organisms, such as *Phaeodactylum tricornutum*, the nucleic acid molecules according to the invention can be used for the recombinant modification of these organisms so that they become better or more efficient producers of one or more fine chemicals. This improved production, or production efficiency, of a fine chemical can be caused by a direct effect of the manipulation of a nucleic acid according to the invention, advantageously in the form of the entire gene, or by an indirect action of this manipulation.

Mosses and algae are the only known plant systems which produce considerable amounts of polyunsaturated fatty acids such as arachidonic acid (ARA) and/or eicosapentaenoic acid (EPA) and/or docosahexaenoic acid (DHA). Fungal systems too, such as Oomycetes (*Eukaryota/Stramenopiles/Oomycetes/Phythiales/Pythiaceaea*) produce the abovementioned fatty acids. This is why nucleic acid molecules which originate from a Oomycete such as *Phytophtohora infestans* are particularly suitable for modifying the lipid and PUFA production system in a host, in particular in microorganisms such as the abovementioned microorganisms, and in plants such as oil crops, for example oilseed rape, canola, linseed, soybeans, sunflowers, borage. Furthermore, nucleic acids from a Oomycete such as *Phytophtohora infestans* can be used for identifying such DNA sequences and enzymes in other species which are suitable for modifying the biosynthesis of PUFA precursor molecules in the organisms in question.

The fungus *Phytophthora infestans* belongs to the Oomycetes. It is related to other fungi which can grow in the absence of light. Fungi such as *Phytophthora* have a high degree of homology with one another at the DNA sequence and polypeptide level, which makes it possible to subject DNA molecules to heterologous screening with probes derived from other fungi or organisms, so that, if further nucleic acid sequences are present in addition to the sequence according to the invention, a consensus sequence which is suitable for the heterologous screening or for the functional commenting and forecasting of gene functions in third species can be derived. However, forecasting the function of the proteins or enzymes encoded by the sequences is not possible as yet. The ability of identifying these functions, for example forecasting the substrate specificity of enzymes, can therefore be of significant importance. Furthermore, these nucleic acid molecules can act as reference sequences for mapping other fungi or for deriving PCR primers.

Moreover, a functionally active PSE gene has been isolated for the first time from the Oomycetes *Phytophthora infestans* (*Eukaryota/Stramenopiles, Oomycetes/Phythiales/Pythiaceaea*). The gene is advantageously suitable for the production of long-chain polyunsaturated fatty acids, preferably those having more than sixteen or eighteen carbon atoms in the carbon skeleton of the fatty acid and/or at least two double bonds in the carbon chain, the enzymes encoded by the sequence according to the invention having a preference for the abovementioned fatty acids during the elongation process.

The novel nucleic acid molecules encode a protein termed in the present context PUFA-specific elongase (=PSEs, or PSE in the singular). These PSEs can, for example, exert a function which is involved in the metabolism (for example in the biosynthesis or in the breakdown) of compounds required for lipid or fatty acid synthesis, such as PUFAs, or which participate in the transmembrane transport of one or more lipid/fatty acid compounds, either into the cell or out of the cell.

This novel application shows the function of the sequence in greater detail. For the first time, we have isolated a functionally active Oomycete gene which is suitable for producing long-chain polyunsaturated fatty acids, preferably having more than sixteen or eighteen carbon atoms in the carbon skeleton of the fatty acid and/or at least two double bonds in the carbon chain, the enzymes encoded by the sequence of the invention showing a preference for the abovementioned fatty acids during the elongation steps. This means a PSE gene or PSE protein. Other publications and patents disclose, or show, no functionally active PSE gene, even though various known patent applications exist which show the elongation of saturated fatty acids of short or medium chain length (WO 98/46776 and U.S. Pat. No. 5,475,099) or the elongation or production of long-chain fatty acids, but which then have no more than one double bond or lead to long-chain fatty acid wax esters (see WO 98/54954, WO 96/13582, WO 95/15387).

While WO 99/64616, WO 98/46763, WO 98/46764, WO 98/46765 describe the production of PUFAs in transgenic plants and demonstrate the cloning and functional expression of corresponding desaturase activities, in particular from fungi, they demonstrate no indispensable PSE-encoding gene and no functional PSE activity. The production of a trienoic acid with $C_{18}$-carbon chain has been demonstrated and claimed with reference to gamma-linolenic acid, but the production of very long-chain polyunsaturated fatty acids (with a $C_{20}$- and longer carbon chain and of trienoic acids and higher unsaturated types) and the substrate specificity of the elongase have, however, not been taught to date.

To prepare long-chain PUFAs, the polyunsaturated $C_{16}$- and/or $C_{18}$-fatty acids must be elongated by at least two carbon atoms by the enzymatic activity of an elongase. The nucleic acid sequence according to the invention encodes the first fungal elongase which is capable of elongating the $C_{16}$- or $C_{18}$-fatty acids with at least two double bonds in the fatty acid by at least two carbon atoms. After one elongation cycle, this enzyme activity leads to $C_{20}$-fatty acids, and after two, three and four elongation cycles to $C_{22}$-, $C_{24}$- oder $C_{26}$-fatty acids. An advantage of the enzymatic activity according to the invention is that not all unsaturated $C_{20}$-fatty acids are elongated. This makes possible the specific synthesis of individual desirable unsaturated fatty acids or fatty acid mixtures. Longer PUFAs can also be synthesized using the elongase according to the invention. The activity of the elongases according to the invention preferably leads to $C_{20}$- and/or $C_{22}$-fatty acids with at least two double bonds in the fatty acid molecule, preferably with three or four double bonds, especially preferred are fatty acids with one double bond in the Δ6 position. After the elongation by the enzymes according to the invention has taken place, further desaturation steps may be carried out. The products of the elongase activity and of the further desaturation which is a possibility therefore lead to preferred PUFAs with a higher degree of desaturation, such as docosadienoic acid, arachidonic acid, ω6-eicosatrienedihomo-γ-linolenic acid, eicosapentenoic acid, ω3-eicosatrienoic acid, ω3-eicosatetraenoic acid, docosapentaenoic acid or docosahexaenoic acid. Substrates of the enzyme activity according to the invention are, for example, taxol acid; 6,9-octadecadienoic acid, linoleic acid, γ-linolenic acid, pinolenic acid, α-linolenic acid or stearidonic acid. Preferred substrates are linolic acid, γ-linolenic acid and/or α-linolenic acid. The $C_{16}$- and/or $C_{18}$-fatty acids with at least two double bonds in the fatty acid can be elongated by the enzymatic activity according to the invention in the form of the free fatty acid or in the form of the esters, such as phospholipids, glycolipids, sphingolipids, phosphoglycerides, monoacylglycerol, diacylglycerol or triacylglycerol.

Using cloning vectors which are suitable for use in plants and in the transformation of plants, such as those which are published in Plant Molecular Biology and Biotechnology (CRC Press, Boca Raton, Fla.), chapter 6/7, pp. 71–119 (1993); F. F. White, Vectors for Gene Transfer in Higher Plants; in: Transgenic Plants, Vol. 1, Engineering and Utilization, Ed.: Kung and R. Wu, Academic Press, 1993, 15–38; B. Jenes et al., Techniques for Gene Transfer, in: Transgenic Plants, Vol. 1, Engineering and Utilization, Ed.: Kung and R. Wu, Academic Press (1993), 128–143; Potrykus, Annu. Rev. Plant Physiol. Plant Molec. Biol. 42 (1991), 205–225)) and in references cited in these publications, the nucleic acids according to the invention can be used for the recombinant modification of a broad spectrum of plants so that they become a better or more efficient producer of one or more lipid-derived products, such as PUFAs. This improved production or production efficiency of a lipid-derived product, such as PUFAs, can be caused by the direct effect of the manipulation or by an indirect effect of this manipulation.

There exists a series of mechanisms by which the modification of a PSE protein according to the invention can directly affect yield, production and/or production efficiency of a fine chemical from an oil crop or a microorganism, owing to a modified protein. The number or activity of the PSE protein, PSE nucleic acid or PSE gene can be increased so that greater quantities of these compounds are produced de novo since the organisms lacked this activity and biosynthesis ability prior to introduction of the nucleic acid gene in question.

The introduction of a nucleic acid according to the invention and/or a PSE gene into an organism or a cell can not only increase the biosynthesis flow toward the end product, but also increase, or create de novo, the corresponding triacylglycerol composition. Equally, the number or activity of other genes which are involved in the import of nutrients required for the biosynthesis of one or more fine chemicals (for example fatty acids, polar and neutral lipids) may be increased, so that the concentration of these precursors, cofactors or intermediates is increased within the cells or within the storage compartment, thus further increasing the ability of the cells to produce PUFAs, as described hereinbelow. Fatty acids and lipids themselves are desirable as fine chemicals; optimization of the activity, or increasing the number, of one or more PSEs which are involved in the biosynthesis of these compounds, or destroying the activity of one or more PSEs which are involved in the breakdown of these compounds, can make possible an increase in yield, production and/or production efficiency of fatty acid molecules and lipid molecules from plants or microorgansims.

The mutagenesis of the PSE gene according to the invention or of the nucleic acid may also lead to a PSE protein with modified activities which directly or indirectly affect the production of one or more desired fine chemicals. For example, the number or activity of the PSE gene according to the invention or of the nucleic acid can be increased, so that the normal metabolic waste products or byproducts of the cell (whose quantity might be increased owing to the overproduction of the desired fine chemical) are exported in an efficient manner before they destroy other molecules or processes within the cell (which would reduce cell viability) or would interfere with the biosynthetic pathways of the fine chemical (thus reducing yield, production or production efficiency of the desired fine chemical). Furthermore, the relatively large intracellular quantities of the desired fine chemical themselves may be toxic to the cell or may interfere with enzyme feedback mechanisms, such as allosteric regulation; for example, they might increase the allocation of the PUFA into the triacylglycerol fraction owing to an increased activity or number of other enzymes or detoxifying enzymes of the PUFA pathway which follow downstream; the viability of seed cells might increase which, in turn, leads to better development of cells in culture or to seeds which produce the desired fine chemical. Alternatively, the PSE gene or nucleic acids according to the invention can be manipulated in such a way that the corresponding quantities of the various lipid molecules and fatty acid molecules are produced. This can have a decisive effect on the lipid composition of the cell membrane and generates novel oils in addition to the occurrence of PUFAs which have been synthesized de novo. Since each type of lipid has different physical properties, a change in the lipid composition of a membrane can substantially modify membrane fluidity. Changes in membrane fluidity can have an effect on the transport of molecules via the membrane and on cell integrity, both of which have a decisive effect on the production of fine chemicals. In plants, moreover, these changes can also have an effect on other traits such as the tolerance to abiotic and biotic stress situations.

Biotic and abiotic stress tolerance is a general trait which it is desirable to impart to a broad spectrum of plants such as maize, wheat, rye, oats, triticale, rice, barley, soybean, peanut, thistle, cotton, oilseed rape and canola, cassava, pepper, sunflower and tagetes, *Solanaceae* plants such as potato, tobacco, aubergine and tomato, *Vicia* species, pea, alfalfa, shrub plants (coffee, cacao, tea), *Salix* species, trees (oil palm, coconut) and perennial grasses and fodder crops. As a further embodiment according to the invention, these crops are also preferred target plants for genetic engineering. Very especially preferred plants according to the invention are oil crops such as soybean, peanut, oilseed rape, canola, sunflower, thistle, trees (oil palm, coconut) or crops such as maize, wheat, rye, oats, triticale, rice, barley, alfalfa, or shrub plants (coffee, cacao, tea).

Accordingly, one aspect of the invention relates to isolated nucleic acid molecules (for example cDNAs) comprising a nucleotide sequence which encodes a PSE or biologically active parts thereof, or nucleic acid fragments which are suitable as primers or hybridization probes for the detection or amplification of PSE-encoding nucleic acids (for example DNA or mRNA). In a specially preferred embodiment, the nucleic acid molecule comprises one of the nucleotide sequences shown in SEQ ID No:1, or the coding region or a complement of one of these nucleotide sequences. In other especially preferred embodiments, the isolated nucleic acid molecule according to the invention comprises a nucleotide sequence which hybridizes with a nucleotide sequence as shown in the sequence SEQ ID NO:1, or a part thereof or which has at least approximately 50%, preferably at least approximately 60%, more preferably at least approximately 70%, 80% or 90% and even more preferably at least approximately 95%, 96%, 97%, 98%, 99% or more homology thereto, homology meaning identity for the purposes of the present invention. In other preferred embodiments, the isolated nucleic acid molecule encodes one of the amino acid sequences shown in the sequence SEQ ID NO:2. Preferably, the preferred PSE gene according to the invention and the nucleic acid sequence according to the invention also has at least one of the PSE activities described herein.

In a further embodiment, the isolated nucleic acid molecule encodes a protein or part thereof, the protein or the part thereof comprising an amino acid sequence which has sufficient homology with an amino acid sequence of the sequence SEQ ID NO:2 that the protein or the part thereof retains a PSE activity, homology meaning identity for the purposes of the present invention. Preferably, the protein or the part thereof which is encoded by the nucleic acid molecule retains the ability to participate in the metabolism of compounds required for the synthesis of cell membranes of plants or in the transport of molecules via these membranes. In one embodiment, the protein encoded by the nucleic acid molecule has at least approximately 50%, preferably at least approximately 60% and more preferably at least approximately 70%, 80% or 90% and most preferably at least approximately 95%, 96%, 97%, 98%, 99% or more homology with an amino acid sequence of the sequence SEQ ID NO:2. In a further preferred embodiment, the protein is a *Phytophthora infestans* full-length protein which is essentially homologous to a complete amino acid sequence of SEQ ID NO:2 (which is due to the open reading frame shown in SEQ ID NO:1).

In another preferred embodiment, the isolated nucleic acid molecule originates from *Phytophthora infestans* and encodes a protein (for example a PSE fusion protein) comprising a biologically active domain which has at least approximately 50% or more homology (identity) with an amino acid sequence of the sequence SEQ ID NO:2 and retains the ability to participate in the fungal metabolism of compounds required for the synthesis of unsaturated fatty acids or in the transport of molecules via membranes or which has at least one of the activities listed in Table I, and also comprises heterologous nucleic acid sequences which encode a heterologous polypeptide or regulatory proteins.

The nucleic acids according to the invention encode proteins which elongate fatty acids selected from the group consisting of $C_{18:2}^{\Delta 9,12}$, $C_{18:3}^{\Delta 4,7,10}$, $C_{18:3}^{\Delta 5,8,11}$, $C_{18:3}^{\Delta 6,9,12}$, $C_{18:3}^{\Delta 7,10,13}$, $C_{18:3}^{\Delta 8,11,14}$, $C_{18:3}^{\Delta 9,12,15}$, $C_{18:4}^{\Delta 6,9,12,15}$, $C_{18:3}^{\Delta 5c,9,12}$ or $C_{16:}^{3\Delta 7,10,13}$, while fatty acids such as $C_{18:3}^{\Delta 5t,9,12}$, $C_{20:3}^{\Delta 8,11,14}$, $C_{20:4}^{\Delta 5,8,11,14}$ and $C_{20:5\Delta 5,8,11,14,17}$ are not elongated. The PSE gene was expressed heterologously in yeast, and various polyunsaturated fatty acids were fed individually and converted by the transformed yeasts. The fatty acid profiles of transgenic yeast were analyzed by means of GLC. The percentage of converted fed fatty acids was calculated as follows: mol % (product)×100/[mol % (starting material)+mol % (product)].

Table I shows fatty acids which are elongated by the enzyme according to the invention.

TABLE I

Fatty acids (in mol %) of yeast cells transformed with the plasmid pYES2 (control) and pY2piPSE1. 18:2, γ-18:3, α-18:3 or 18:4 fatty acids were fed. The entire lipid fraction was transmethylated and the fatty acid profile was determined by GC. Calculation of the elongation in %:
100 × mol % (product)/[mol % (starting material) + mol % (product)].
Substrates and elongated fatty acids are printed in bold.

| | % of total fatty acids | | | | | | | |
|---|---|---|---|---|---|---|---|---|
| | PYES2 | | | | PY2piPSE1 | | | |
| Fatty acids | +18:2 | +γ-18:3 | +α-18:3 | +18:4 | +18:2 | +γ-18:3 | +α-18:3 | +18:4 |
| 16:0 | 13.7 | 16.4 | 14.3 | 19.5 | 9.8 | 9.8 | 7.3 | 10.6 |
| $16:1^{\Delta 9}$ | 8.8 | 6.5 | 3.4 | 7.8 | 9.9 | 4.1 | 1.3 | 2.3 |
| 18:0 | 6.9 | 9.9 | 11.3 | 13.3 | 8.6 | 12.3 | 14.4 | 19.4 |
| $18:1^{\Delta 9}$ | 9.9 | 10.5 | 6.0 | 13.6 | 15.3 | 11.8 | 5.6 | 8.4 |
| $18:2^{\Delta 9,12}$ | 60.7 | — | — | — | 41.0 | — | — | — |
| $18:3^{\Delta 6,9,12}$ | — | 56.7 | — | — | — | 51.1 | — | — |
| $18:3^{\Delta 9,12,15}$ | — | — | 64.7 | — | — | — | 65.1 | — |
| $18:4^{\Delta 6,9,12,15}$ | — | — | — | 45.7 | — | — | — | 48.3 |
| $20:2^{\Delta 11,14}$ | — | — | — | — | 2.1 | — | — | — |
| $20:3^{\Delta 8,11,14}$ | — | — | — | — | — | 11.0 | — | — |
| $20:3^{\Delta 11,14,17}$ | — | — | — | — | — | — | 6.2 | — |
| $20:4^{\Delta 8,11,14,17}$ | — | — | — | — | — | — | — | 11.0 |
| % elongation | n.d. | n.d. | n.d. | n.d. | 4.9 | 17.7 | 8.7 | 18.5 |

In another embodiment, the isolated nucleic acid molecule is at least 15 nucleotides in length and hybridizes under stringent conditions with a nucleic acid molecule comprising a nucleotide sequence of SEQ ID NO:1. The isolated nucleic acid molecule preferably corresponds to a naturally occurring nucleic acid molecule. More preferably, the isolated nucleic acid molecule encodes naturally occurring *Phytophthora infestans* PSE or a biologically active part thereof.

A further aspect of the invention relates to vectors, for example recombinant expression vectors, comprising at least one nucleotide molecule according to the invention and host cells into which these vectors have been introduced, in particular microorganisms, plant cells, plant tissues, plant organs or intact plants. Nonhuman host cells, such as, for example, *Caenorhabditis elegans* can also be used advantageously. In one embodiment, such a host cell can store fine chemicals, in particular PUFAs; to isolate the desired compound, the cells are harvested. The compound (oils, lipids, triacylglycerides, fatty acids) or the PSE can then be isolated from the medium or from the host cell which, in the case of plants, are cells comprising or storing the fine chemicals, most preferably cells of storage tissues such as seed coats, tubers, epidermis cells and seed cells.

Yet another aspect of the invention relates to a genetically modified plant (=transgenic plant), preferably an oil crop as mentioned above, or a genetically modified fungus (=transgenic fungus), especially preferably a fungus of the genus *Phytophthora* or a plant into which a PSE gene, preferably from an Oomycete such as, advantageously, *Phytophthora infestans*, has been introduced or in which a PSE gene has been modified. In one embodiment, the genome of *Phytophthora infestans* has been modified by introducing, as transgene, a nucleic acid molecule according to the invention encoding a wild-type or mutated PSE sequence. In another embodiment, an endogenous PSE gene in the genome of the Oomycete *Phytophthora infestans* has been modified, that is to say functionally destroyed, by homologous recombination with a modified PSE gene. In a preferred embodiment, the plant organism belongs to the genus *Physcomitrella, Ceratodon* or *Funaria*, with *Physcomitrella* being preferred. In a preferred embodiment, the *Physcomitrella* plant is also used to produce a desired compound such as lipids or fatty acids, with PUFAs being especially preferred.

In yet another preferred embodiment, the Oomycete Phytophthora infestans can be used for demonstrating a function of a moss gene using homologous recombination on the basis of the nucleic acids described in the patent invention.

Yet another aspect of the invention relates to an isolated nucleic acid sequence, a PSE gene or part, for example a biologically active part, thereof. In a preferred embodiment, the isolated nucleic acid sequence, the PSE, or part thereof can participate in the metabolism of compounds required for the synthesis of cell membranes in a microorganism or a plant cell or in the transport of molecules via its membranes. In a further preferred embodiment, the isolated nucleic acid sequence, the PSE or the part thereof has sufficient homology with an amino acid sequence of SEQ ID NO:2, for this protein or part thereof to retain the ability to participate in the metabolism of compounds required for the synthesis of cell membranes in microorganisms or plant cells or in the transport of molecules via these membranes.

The invention also provides an isolated preparation of a PSE (PSE protein). In preferred embodiments, the nucleic acid sequence of the invention or the PSE gene comprises an amino acid sequence of SEQ ID NO:2. In a further preferred embodiment, the invention relates to an isolated full-length protein which is essentially homologous with a complete amino acid sequence of SEQ ID NO:2 (which is encoded by the open reading frame shown in SEQ ID NO:1). In a further embodiment, the protein has at least approximately 50%, preferably at least 60%, more preferably at least approximately 70%, 80% or 90% and most preferably at least approximately 95%, 96%, 97%, 98%, 99% or more homology (=identity) with an amino acid sequence of sequence SEQ ID NO:2. In other embodiments, the isolated nucleic acid sequence and the PSE comprise an amino acid sequence which has at least approximately 50% homology with one of the amino acid sequences of SEQ ID NO:2 and which can participate in the metabolism of compounds required for the synthesis of fatty acids in a microorganism or a plant cell or in the transport of molecules via these membranes or has one or more of the PUFA-elongating activities, the elongation advantageously relating to desaturated $C_{16}$- and/or $C_{18}$-carbon chains with double bonds in at least two positions.

As an alternative, the isolated PSE protein can comprise an amino acid sequence which is encoded by a nucleotide sequence hybridizing with a nucleotide sequence of SEQ ID NO:1, for example under stringent conditions, or which has at least approximately 50%, preferably at least approximately 60%, more preferably at least approximately 70%, 80% or 90% and even more preferably at least approximately 95%, 96%, 97%, 98%, 99% or more homology thereto. It is also preferred for the preferred PSE forms also to have one of the PSE activities described herein.

The PSE polypeptide or a biologically active part thereof can be linked functionally to a non-PSE polypeptide to form a fusion protein. In preferred embodiments, this fusion protein has an activity which differs from that of PSE alone. In other preferred embodiments, this fusion protein participates in the metabolism of compounds which are advantageously required for the synthesis of lipids and fatty acids, cofactors and enzymes in microorganisms or plants, or in the transport of molecules via these membranes. In especially preferred embodiments, the introduction of this fusion protein into a host cell modulates the production of a desired compound, such as, advantageously, the synthesis of PUFAs by the cell. In a preferred embodiment, these fusion proteins also contain Δ-4-, Δ-5- or Δ-6-desaturase activities, alone or in combination.

Another aspect of the invention relates to a process for the production of a fine chemical advantageously from unsaturated fatty acids and/or lipids unsaturated fatty acids. This process either comprises culturing a suitable microorganism or culturing plant cells, plant tissues, plant organs or intact plants comprising the nucleotide sequence according to the invention of SEQ ID NO: 1 or its homologs, derivatives or analogs or a gene construct which comprises SEQ ID NO: 1 or its homologs, derivatives or analogs, or a vector comprising these sequences or the gene construct which brings about the expression of a PSE nucleic acid molecule according to the invention so that a fine chemical is produced. In a preferred embodiment, the process furthermore comprises the step of obtaining a cell comprising such an elongase nucleic acid sequence according to the invention, in which a cell is transformed with an elongase nucleic acid sequence, a gene construct or a vector which bring about the expression of a PSE nucleic acid according to the invention. In a further preferred embodiment, this process furthermore comprises the step of obtaining the fine chemical from the culture. In an especially preferred embodiment, the cell belongs to the order of the *Ciliata*, to microorganisms such as fungi, or to the plant kingdom, in particular to oil crops, with microorganisms or oil crops being especially preferred.

A further aspect of the invention relates to methods of modulating the production of a molecule by a microorganism. These methods comprise combining the cell with a substance which modulates the PSE activity or the expression of the PSE nucleic acid so that a cell-associated activity is modified relative to the same activity in the absence of the substance. In a preferred embodiment, a metabolic pathway, or two metabolic pathways, (e), of the cell for lipids and fatty acids, cofactors and enzymes is, or are, modulated or the transport of compounds via these membranes is modulated so that the yield or the production rate of a desired fine chemical by this microorganism is improved. The substance which modulates the PSE activity can be a substance which stimulates the PSE activity or the expression of the PSE nucleic acid or which can be used as intermediate in fatty acid biosynthesis. Examples of substances which stimulate the PSE activity or the expression of PSE nucleic acids are, inter alia, small molecules, active PSEs and nucleic acids encoding PSEs which have been introduced into the cell. Examples of substances which inhibit the PSE activity or PSE expression are, inter alia, small molecules and antisense PSE nucleic acid molecules.

A further aspect of the invention relates to methods of modulating the yields of a desired compound from a cell, which comprise introducing, into a cell, a wild-type or mutant PSE gene or a wild-type or mutant nucleic acid of the invention which is either kept on a separate plasmid or integrated into the genome of the host cell. In the case of integration into the genome, integration can be random or take place by recombination in such a way that the native nucleic acid sequence or the native gene is replaced by the copy which is introduced, thus modulating the production of the desired compound by the cell, or by using a gene in trans, so that the gene is functionally linked to a functional expression unit comprising at least one sequence which facilitates the expression of a gene and at least one sequence which facilitates the polyadenylation of a functionally transcribed gene or of the nucleic acid.

In a preferred embodiment, the yields are modified. In a further embodiment, the desired chemical is increased, it being possible to reduce undesired compounds which have a negative effect. In an especially preferred embodiment, the desired fine chemical is a lipid or fatty acid, a cofactor or an enzyme. In an especially preferred embodiment, this chemical is a polyunsaturated fatty acid. More preferably, it is selected from amongst arachidonic acid (ARA), eicosapentaenoic acid (EPA) or docosahexaenoic acid (DHA).

DETAILED DESCRIPTION OF THE INVENTION

The present invention provides a PSE nucleic acid and a protein molecule which participate in the metabolism of lipids and fatty acids, PUFA cofactors and enzymes in Oomycete *Phytophthora infestans* or in the transport of lipophilic compounds via membranes. The compounds according to the invention can be used for modulating the production of fine chemicals from organisms, for example microorganisms, such as ciliates, fungi, yeasts, bacteria, algae, and/or plants such as maize, wheat, rye, oats, triticale, rice, barley, soybean, peanut, cotton, thistle, *Brassica* species, such as oilseed rape, thistle, canola and turnip rape, pepper, sunflower, borage, evening primrose and tagetes, *Solanaceae* plants such as potato, tobacco, aubergine and tomato, *Vicia* species, pea, cassava, alfalfa, shrub plants (coffee, cacao, tea), *Salix* species, trees (oil palm, coconut) and perennial grasses and fodder crops, either directly (for example when the overexpression or optimization of a fatty acid biosynthesis protein has a direct influence on the yield, production and/or production efficiency of the fatty acid from modified organisms) or they can have an indirect effect which nevertheless leads to an increased yield, production and/or production efficiency of a desired compound or to a decrease in undesired compounds (for example when the modulation of the lipid and fatty acid, cofactor and enzyme metabolism leads to changes in yield, production and/or production efficacy or in the composition of the desired compounds within the cells, which, in turn, may affect the production of one or more fine chemicals). Aspects of the invention are illustrated in greater detail hereinbelow.

I. Fine Chemicals and PUFAs

The term "fine chemicals" is known in the art and comprises molecules which have been produced by an organism and which are used in a variety of industries such as, by way of example but not by way of limitation, the pharmaceuticals industry, agroindustry, food industry and cosmetics industry. These compounds comprise lipids, fatty acids, cofactors and enzymes and the like (as described, for example, in Kuninaka, A. (1996) Nucleotides and related compounds, pp. 561–612, in Biotechnology Vol. 6, Rehm et al., Ed.: VCH Weinheim and references cited therein), lipids, saturated and unsaturated fatty acids (for example arachidonic acid), vitamins and cofactors (as described in Ullmann's Encyclopedia of Industrial Chemistry, Vol. A27, Vitamins, pp. 443–613 (1996): VCH Weinheim, and references cited therein; and Ong, A. S., Niki, E., & Packer, L. (1995) Nutrition, Lipids, Health and Disease Proceedings of the UNESCO/Confederation of Scientific and Technological Associations in Malaysia and the Society for Free Radical Research—Asia, held Sep. 1–3, 1994 in Penang, Malaysia, AOCS Press (1995)), enzymes and all other chemicals described by Gutcho (1983) in Chemicals by Fermentation, Noyes Data Corporation, ISBN: 0818805086 and references cited therein. The metabolism and the uses of certain fine chemicals are illustrated in greater detail hereinbelow.

The combination of various precursor molecules and biosynthetic enzymes leads to the production of various fatty acid molecules, which has a decisive effect on membrane composition. It can be assumed that PUFAs are not only just incorporated into triacylglycerol, but also into membrane lipids.

Membrane synthesis is a well characterized process in which a number of components, inclusive of lipids as part of the bilayer membrane, are involved. The production of novel fatty acids such as PUFAs can therefore generate novel properties of membrane functions within a cell or an organism.

Cell membranes serve a multiplicity of functions in a cell. First and foremost, a membrane delimits the contents of a cell from the environment, thus imparting integrity to the cell. Membranes can also act as barriers against the influx of dangerous or undesired compounds or else against the efflux of desired compounds.

For more detailed descriptions and involvements of membranes and the mechanisms involved, see Bamberg, E., et al. (1993) Charge transport of ion pumps on lipid bilayer membranes, Q. Rev. Biophys. 26:1–25; Gennis, R. B. (1989) Pores, Channels and Transporters, in: Biomembranes, Molecular Structure and Function, Springer: Heidelberg, pp. 270–322; and Nikaido, H., und Saier, H. (1992) Transport proteins in bacteria: common themes in their design, Science 258:936–942, and the citations contained in each of these references.

Lipid synthesis can be divided into two parts: the synthesis of fatty acids and their binding to sn-glycerol-3-phosphate, and the addition or modification of a polar head group. Customary lipids used in membranes comprise phospholipids, glycolipids, sphingolipids and phosphoglycerides. Fatty acid synthesis starts with the conversion of acetyl-CoA either into malonyl-CoA by acetyl-CoA carboxylase or into acetyl-ACP by acetyl transacylase. After a condensation reaction, these two product molecules together form acetoacetyl-ACP, which is converted via a series of condensation, reduction and dehydration reactions to give a saturated fatty acid molecule with the desired chain length. The production of the unsaturated fatty acids from these molecules is catalyzed by specific desaturases, either aerobically by means of molecular oxygen or anaerobically (as regards fatty acid synthesis in microorganisms, see F. C. Neidhardt et al. (1996) E. coli and Salmonella. ASM Press: Washington, D.C., pp. 612–636 and references contained therein; Lengeler et al. (Ed.) (1999) Biology of Procaryotes. Thieme: Stuttgart, N.Y., and the references contained therein, and Magnuson, K., et al. (1993) Microbiological Reviews 57:522–542 and the references contained therein).

Examples of precursors for PUFA biosynthesis are palmitoleic, linolic and linolenic acid. Thse $C_{16}$- and/or $C_{18}$-carbon fatty acids must be elongated to $C_{20}$ and $C_{22}$ to give fatty acids of the eicosa and docosa chain type. This elongation is preferably effected with the aid of the nucleic acids according to the invention, of the proteins encoded by these nucleic acids. Various desaturases such as enzymes which have Δ-6-desaturase, Δ-5- and Δ-4-desaturase activity can lead to arachidonic acid, eicosapentenoic acid and docosahexaenoic acid and various other long-chain PUFAs which can be extracted and used for various purposes in food and feed, cosmetic or pharmaceutical applications.

To produce long-chain PUFAs, the polyunsaturated $C_{16}$- and/or $C_{18}$-fatty acids must, as mentioned above, be elongated by at least two carbon atoms by the enzymatic activity of an elongase. The nucleic acid sequences according to the invention encode first plant elongases which are capable of elongating the $C_{16}$- and/or $C_{18}$-fatty acids with at least two double bonds in the fatty acid by at least two carbon atoms. After one elongation cycle, this enzyme activity leads to $C_{18}$- or $C_{20}$-fatty acids, and after two, three and four or five elongation cycles to $C_{22}$-, $C_{24}$- or $C_{26}$-fatty acids. Longer PUFAs can also be synthesized with the elongases according to the invention. The activity of the elongases according to the invention preferably leads to $C_{20}$- and/or $C_{22}$-fatty acids with at least two double bonds in the fatty acid molecule, preferably with three or four double bonds, especially preferably three double bonds, in the fatty acid molecule. After elongation with the enzymes according to the invention, further desaturation steps may be carried out. Thus, the products of the elongase activities and of the further desaturation which is possible lead to preferred PUFAs with a higher degree of desaturation, such as docosadienoic acid, arachidonic acid, ω6-eicosatrienedihomo-γ-linolenic acid, eicosapentenoic acid, (ω3-eicosatrienoic acid, (ω3-eicosatetraenoic acid, docosapentaenoic acid or docosahexaenoic acid. Examples of substrates of this enzyme activity according to the invention are taxol acid, 6,9-octadecadienoic acid, linoleic acid, γ-linolenic acid, pinolenic acid, α-linolenic acid or stearidonic acid. Preferred substrates are linolic acid, γ-linolenic acid and/or α-linolenic acid. The $C_{16}$- and/or $C_{18}$-fatty acids with at least two double bonds in the fatty acid can be elongated by the enzyme activity according to the invention in the form of the free fatty acid or in the form of the esters, such as phospholipids, glycolipids, sphingolipids, phosphoglycerides, monoacylglycerol, diacylglycerol or triacylglycerol.

Furthermore, fatty acids must subsequently be transported to various modifications and incorporated into the triacylglycerol storage lipid. Another important step in lipid synthesis is the transfer of fatty acids to the polar head groups, for example by glycerol fatty acid acyltransferase (see Frentzen, 1998, Lipid, 100(4–5):161–166).

Moreover, the expression of the nucleic acids according to the invention in the various host organisms causes not only a change in the composition of the membrane lipids in total, but the composition of all compounds in the host cell which comprise unsaturated fatty acids is modified over the original host cells which do not comprise the nucleic acids, or which do not comprise them in such amounts. These modifications are more pronounced in host organisms, for example plant cells, which do not naturally comprise the proteins, or enzymes, encoded by the nucleic acids. Expression of the nucleic acids thus gives rise to novel liquid compositions, which are a further aspect of the invention.

For publications about the plant-fatty acid biosynthesis, desaturation, the lipid metabolism and membrane transport of fatty compounds, beta-oxidation, fatty acid modification and cofactors, triacylglycerol storage and assembly inclusive of the references cited therein, see the following articles: Kinney, 1997, Genetic Engineering, Ed.: J K Setlow, 19:149–166; Ohlrogge and Browse, 1995, Plant Cell 7:957–970; Shanklin and Cahoon, 1998, Annu. Rev. Plant Physiol. Plant Mol. Biol. 49:611–641; Voelker, 1996, Genetic Engineering, Ed.: J K Setlow, 18:111–13; Gerhardt, 1992, Prog. Lipid R. 31:397–417; Gühnemann-Schäfer & Kindl, 1995, Biochim. Biophys Acta 1256:181–186; Kunau et al., 1995, Prog. Lipid Res. 34:267–342; Stymne et al., 1993, in: Biochemistry and Molecular Biology of Membrane and Storage Lipids of Plants, Ed.: Murata and Somerville, Rockville, American Society of Plant Physiologists, 150–158, Murphy & Ross 1998, Plant Journal. 13(1):1–16.

Vitamins, cofactors and "nutraceuticals", such as PUFAs, comprise a group of molecules which higher animals can no longer synthesize and therefore have to take up, or which higher animals can no longer synthesize themselves to a sufficient degree and must therefore take up additionally, even though they are readily synthesized by other organisms such as bacteria. The biosynthesis of these molecules in organisms which are capable of producing them, such as in bacteria, has been more or less characterized (Ullmann's Encyclopedia of Industrial Chemistry, "Vitamins", Vol. A27, pp. 443–613, VCH Weinheim, 1996; Michal, G. (1999) Biochemical Pathways: An Atlas of Biochemistry and Molecular Biology, John Wiley & Sons; Ong, A. S., Niki, E., & Packer, L. (1995) "Nutrition, Lipids, Health and Disease" Proceedings of the UNESCO/Confederation of Scientific and Technological Associations in Malaysia and the Society for Free Radical Research Asia, held Sep. 1–3, 1994, in Penang, Malaysia, AOCS Press, Champaign, IL X, 374 pp).

The abovementioned molecules are either biologically active molecules themselves or precursors of biologically active substances which act either as electron carriers or as intermediates in a multiplicity of metabolic pathways. Besides their nutritional value, these compounds also have a significant industrial value as colorants, antioxidants and catalysts or other processing auxiliaries. (For an overview of structure, activity and industrial applications of these compounds, see, for example, Ullmann's Encyclopedia of Industrial Chemistry, "Vitamins", Vol. A27, pp. 443–613, VCH Weinheim, 1996). Polyunsaturated fatty acids have a variety of functions and health-promoting effects, for example in the case of coronary heart disease, inflammatory mechanisms, children's nutrition and the like. For publications and references including the references cited therein, see: Simopoulos, 1999, Am. J. Clin. Nutr. 70 (3rd Suppl.):560–569, Takahata et al., Biosc. Biotechnol. Biochem. 1998, 62(11): 2079–2085, Willich and Winther, 1995, Deutsche Medizinische Wochenschrift 120(7):229 et seq. They are furthermore important starting materials for the synthesis of compounds which control important biological processes within the organism. They are therefore used for example in a variety of diet foods or in medicaments.

II. Elements and Processes of the Invention

The present invention is based at least in part on the discovery of novel molecules termed herein PSE nucleic acid and PSE protein molecules, which exert an effect on the production of cell membranes or fatty acids as in *Physcomitrella patens, Ceratodon purpureus* and/or *Phytophthora infestans* and, for example, have an effect on the movement of molecules via these membranes. In one embodiment, the PSE molecules participate in the metabolism of compounds required for the synthesis of cell membranes and/or fatty acids in organisms such as microorganisms and plants or indirectly affect the transport of molecules via these membranes. In a preferred embodiment, the activity of the PSE molecules according to the invention for regulating the production of membrane components and membrane transport has an effect on the production of the desired fine chemical by this organism. In an especially preferred embodiment, the activity of the PSE molecules according to the invention is modulated so that the yield, production and/or production efficiency of the metabolic pathways of microorganisms or plants which regulate the PSEs according to the invention are modulated and the transport efficiency of compounds through the membranes is modified, which either directly or indirectly modulates the yield, production and/or production efficiency of a desired fine chemical by microorganisms and plants.

The term PSE or PSE polypeptide comprises proteins which participate in the metabolism of compounds required for the synthesis of cell membranes in organisms such as microorganisms and plants or in the transport of molecules via these membranes. Examples of PSEs are disclosed in SEQ ID NO:1 or its homologs, derivatives or analogs. The terms PSE or PSE nucleic acid sequence(s) comprise nucleic acid sequences which encode a PSE and part of which is a coding region and also corresponding 5'- and 3'-untranslated sequence regions. Examples of PSE genes are the sequences shown in SEQ ID NO:1. The terms production and productivity are known in the art and comprise the concentration of the fermentation product (for example of the desired fine chemical) which is formed within a certain period and in a certain fermentation volume (for example kg product per hour per liter). The term production efficiency comprises the time required for achieving a particular product quantity (for example the time required by the cell to establish a particular throughput rate of a fine chemical). The term yield or product/carbon yield is known in the art and comprises the efficiency with which the carbon source is converted into the product (i.e. the fine chemical). This is usually expressed as, for example, kg product per kg carbon source. Increasing the yield or production of the compound increases the amount of the molecules obtained or of the suitable molecules of this compound obtained in a specific quantity of culture over a defined period. The terms biosynthesis or biosynthetic pathway are known in the art and comprise the synthesis of a compound, preferably of an organic compound, by a cell from intermediates, for example in a multi-step process which is subject to strong regulation. The terms catabolism or catabolic pathway are known in the art and comprise the cleavage of a compound, preferably of an organic compound, by a cell into catabolites (in general smaller or less complex molecules), for example in a multi-step process which is subject to strong regulation. The term metabolism is known in the art and comprises the totality of the biochemical reactions which take place in an organism. The metabolism of a certain compound (for example the metabolism of a fatty acid) thus comprises the totality of the biosynthetic, modification and catabolic pathways of this compound in the cell which are relevant to this compound.

In another embodiment, the PSE molecules according to the invention can modulate the production of a desired molecule, such as a fine chemical, in a microorganism or in plants. There exists a series of mechanisms by which the modification of a PSR according to the invention can directly affect the yield, production and/or production efficiency of a fine chemical from a microorganism strain or plant strain comprising this modified protein. The number or activity of PSEs participating in the transport of molecules of fine chemicals within, or out of, the cell can be increased, so that greater amounts of these compounds are transported via membranes, from which they can be obtained and converted into each other with greater ease. Furthermore, fatty acids, triacylglycerols and/or lipids are desirable fine chemicals themselves; optimizing the activity or increasing the number of one or more PSEs according to the invention which participate in the biosynthesis of these compounds, or interfering with the activity of one or more PSEs which participate in the catabolism of these compounds makes increasing the yield, production and/or production efficiency of fatty acid molecules and lipid molecules from organisms such as microorganisms or plants, possible.

The mutagenesis of the nucleic acids or PSE genes according to the invention can also give rise to PSEs with modified activities which indirectly affect the production of one or more desired fine chemicals from microorganisms or plants. For example, PSEs according to the invention which participate in the export of waste products can exhibit a greater number or higher activity, so that the normal metabolic waste products of the cell (whose quantity might be increased owing to the overproduction of the desired fine chemical) are exported efficiently before they can damage the molecules in the cell (which would reduce the cell's viability) or interfere with the biosynthetic pathways of the fine chemicals (which would reduce the yield, production or production efficiency of a desired fine chemical). The relatively large intracellular amounts of the desired fine chemical themselves can furthermore be toxic to the cell, so that increasing the activity or number of transporters capable of exporting these compounds from the cell results in an increased viability of the cell in culture, which, in turn, leads to a higher number of cells in the culture which produce the desired fine chemical. The PSEs according to the invention can also be manipulated in such a way that the corresponding amounts of different lipid molecules and fatty acid molecules are produced. This can have a substantial effect on the lipid composition of the cell membrane. Since each lipid type has different physical properties, a modification of the lipid composition of a membrane can significantly modify membrane fluidity. Modifications of the membrane fluidity can affect the transport of molecules via the membrane and cell integrity, each of which has a substantial effect on the production of fine chemicals from microorganisms and plants in large-scale fermentation culture. Plant membranes impart specific properties such as tolerance to high and low temperatures, salt, drought and tolerance with respect to pathogens such as bacteria and fungi. The modulation of the membrane components may therefore have a critical effect on the ability of the plants to survive under the abovementioned stress parameters. This can take place via changes in signal cascades or directly via the modified membrane composition (see, for example, Chapman, 1998, Trends in Plant Science, 3(11):419–426) and signal cascades (see Wang 1999, Plant Physiology, 120:645–651) or affect the tolerance of low temperatures, as disclosed in WO 95/18222.

The isolated nucleic acid sequences according to the invention are present in the genome of a *Phytophthora infestans* strain which is available, for example, via the collections ATCC or DSM. The nucleotide sequence of the isolated *Physcomitrella patens* cDNA and the derived amino acid sequences of the *Phytophthora infestans* PSEs are shown in SEQ ID NO:1 and 2, respectively. Computer analyses were carried out which classify and/or identify these nucleotide sequences as sequences which encode proteins participating in the metabolism of cell membrane components or which participate in the transport of compounds via cell membranes or fatty acids. An EST with the database input No. 08_ck19_b07 of the inventor is part of the sequence shown in SEQ ID NO:1. In the meantime these ESTs were renamed, which led to the revised name: pp001019019f. In a similar manner the partial polypeptide was named as pp001019019f. The complete fragment-insert of the EST pp001019019f was sequenced and resulted in SEQ ID NO:1, which shows the complete sequence of pp001019019f. It comprises a complete, functionally active clone which emerged, after specific expression in yeast, to have the desired substrate specificity as shown in the examples section. Yeasts too are suitable organisms according to the invention, for example as host cells for the genes, gene constructs or vectors according to the invention.

The present invention also relates to proteins with an amino acid sequence which is essentially homologous with (identical to) an amino acid sequence of SEQ ID NO:2. As used in the present context, a protein with an amino acid sequence which is essentially homologous with a selected amino acid sequence has at least approximately 50% homology with the selected amino acid sequence, for example the complete amino acid sequence selected. A protein with an amino acid sequence which is essentially homologous with a selected amino acid sequence can also have at least approximately 50 to 60%, preferably at least approximately 60 to 70%, more preferably at least approximately 70 to 80%, 80 to 90% or 90 to 95%, and most preferably at least approximately 96%, 97%, 98%, 99% or more homology with a selected amino acid sequence.

The PSE according to the invention or the biologically active part or the fragment thereof can participate in the metabolism of compounds required for the synthesis of cell membranes in microorganisms or plants or in the transport of molecules via these membranes or have one or more of the activities required for the elongation of $C_{18}$-PUFAs so that $C_{22}$- or $C_{24}$-PUFAs and related PUFAs are obtained.

Various aspects of the invention are described in greater detail in the subsections which follow.

A. Isolated Nucleic Acid Molecules

One embodiment of the invention comprises an isolated nucleic acid derived from an Oomycete strain and encoding a polypeptide which elongates a $C_{16}$- and/or $C_{18}$-fatty acid with at least two double bonds in the fatty acid by at least two carbon atoms.

A further embodiment according to the invention is an isolated nucleic acid comprising a nucleotide sequence encoding a polypeptide which elongates $C_{16}$- and/or $C_{18}$-fatty acids with at least two double bonds in the fatty acid, selected from the group consisting of a) a nucleic acid sequence shown in SEQ ID NO:1,
b) a nucleic acid sequence which, in accordance with the degeneracy of the genetic code, is derived from the sequence shown in SEQ ID NO:1,
c) derivatives of the sequence shown in SEQ ID NO:1 which encode polypeptides with at least 50% homology with the sequence encoding the amino acid sequences in SEQ ID NO:2, the sequence acting as $C_{16}$- or $C_{18}$-elongase.

The abovementioned nucleic acid is derived from organisms such as ciliates, fungi, algae or dinoflagellates which are capable of synthesizing PUFAs, preferably from plants or fungi, especially preferably from the genus *Phytophthora*, and most preferably from *Phytophthora infestans*.

One aspect of the invention relates to isolated nucleic acid molecules which encode PSE polypeptides or biologically active parts thereof, and to nucleic acid fragments which suffice for use as hybridization probes or primers for identifying or amplifying a PSE-encoding nucleic acid (for example PSE DNA). The term "nucleic acid molecule" as used in the present context is intended to comprise single- or double-stranded DNA molecules (for example cDNA or genomic DNA) and RNA molecules (for example mRNA) and DNA or RNA analogs which are generated by means of nucleotide analogs, or DNA/RNA hybrids. This term additionally comprises the untranslated sequence at the 3' and the 5' end of the coding gene region: at least approximately 100 nucleotides of the sequence upstream of the 5' end of the coding region and at least approximately 20 nucleotides of the sequence downstream of the 3' end of the coding gene region. The nucleic acid molecule can be single- or double-stranded, but is preferably double-stranded DNA. An "isolated" nucleic acid molecule is separated from other nucleic acid molecules which are present in the natural source of the nucleic acid. An "isolated" nucleic acid preferably has no sequences which naturally flank the nucleic acid in the genomic DNA of the organism from which the nucleic acid is derived (for example sequences located at the 5' and 3' ends of the nucleic acid). In various embodiments, the isolated PSE nucleic acid molecule can contain, for example, less than approximately 5 kb, 4 kb, 3 kb, 2 kb, 1 kb, 0.5 kb or 0.1 kb nucleotide sequences which naturally flank the nucleic acid molecule in the genomic DNA of the cell from which the nucleic acid is derived (for example a *Physcomitrella patens* cell). An "isolated" nucleic acid molecule, such as a cDNA molecule, can moreover be essentially free from other cellular material or culture medium if it is generated by recombinant techniques, or free from chemical precursors or other chemicals if it is synthesized chemically.

A nucleic acid molecule according to the invention, for example a nucleic acid molecule with a nucleotide sequence of SEQ ID NO:1 or a part thereof, can be isolated using standard techniques of molecular biology and the sequence information provided herein. For example, a *Phytophthora infestans* cDNA can be isolated from a *P. infestans* library by using the complete SEQ ID NO:1 or part thereof as hybridization probe and standard hybridization techniques (such as, for example, as described in Sambrook et al., Molecular Cloning: A Laboratory Manual. 2nd Ed., Cold Spring Harbor Laboratory, Cold Spring Harbor Laboratory Press, Cold Spring Harbor, N.Y., 1989). Moreover, a nucleic acid molecule comprising a complete sequence of SEQ ID NO:1 or a part thereof can be isolated by polymerase chain reaction, where oligonucleotide primers which are generated on the basis of this sequence or parts thereof, in particular regions around His-Box motifs, see Shanklin et al. (1994) Biochemistry 33, 12787–12794, can be used (for example, a nucleic acid molecule comprising the complete sequence of SEQ ID NO:1 or a part thereof can be isolated by polymerase chain reaction using oligonucleotide primers which have been generated on the basis of this same sequence of SEQ ID NO:1). For example, mRNA can be isolated from Oomycete cells (for example by the guanidinium thiocyanate extraction method by Chirgwin et al. (1979) Biochemistry 18:5294–5299), and cDNA can be generated by means of reverse transcriptase (for example Moloney MLV reverse transcriptase, available from Gibco/BRL, Bethesda, Md., or AMV reverse transcriptase, available from Seikagaku America, Inc., St. Petersburg, Fla.). Synthetic oligonucleotide primers for amplification by means of polymerase chain reaction can be generated on the basis of one of the nucleotide sequences shown in SEQ ID NO:1. A nucleic acid according to the invention can be amplified using cDNA or, alternatively, using genomic DNA as template and suitable oligonucleotide primers, in accordance with standard PCR amplification techniques. The nucleic acid thus amplified can be cloned into a suitable vector and characterized by means of DNA sequence analysis. Oligonucleotides which correspond to a PSE nucleotide sequence can be generated by standard synthesis methods, for example with an automatic DNA synthesizer.

The cDNA shown in SEQ ID NO:1 comprises sequences which encode PSEs (i.e. the "coding region") and also 5'-untranslated sequences and 3'-untranslated sequences. Alternatively, the nucleic acid molecule can only comprise the coding region of one of the sequences in SEQ ID NO:1 or can comprise complete genomic fragments isolated from genomic DNA.

In a further preferred embodiment, an isolated nucleic acid molecule according to the invention comprises a nucleic acid molecule which is a complement of one of the nucleotide sequences shown in SEQ ID NO:1 or of a part thereof. A nucleic acid molecule which is complementary to one of the nucleotide sequences shown in SEQ ID NO:1 is a nucleic acid molecule which is sufficiently complementary to one of the nucleotide sequences shown in SEQ ID NO:1 in order to hybridize with one of the sequences stated in SEQ ID NO:1, thereby forming a stable duplex.

Homologs of the new elongase nucleic acid sequences with the sequence SEQ ID NO:1 means, for example, allelic variants with at least approximately 50 to 60%, preferably at least approximately 60 to 70%, more preferably at least approximately 70 to 80%, 80 to 90% or 90 to 95%, and even more preferably at least approximately 95%, 96%, 97%, 98%, 99% or more homology with one of the nucleotide sequences shown in SEQ ID NO:1 or their homologs, derivatives or analogs or parts thereof, homology meaning identity in the context of the invention. In a further preferred embodiment, an isolated nucleic acid molecule according to the invention comprises a nucleotide sequence which hybridizes with one of the nucleotide sequences shown in SEQ ID NO:1 or a part thereof, for example under stringent conditions. Allelic variants comprise, in particular, functional variants which can be obtained by the deletion, insertion or substitution of nucleotides from/into the sequence shown in SEQ ID NO:1, it being intended, however, for the enzyme activity of the resulting proteins which are synthesized to be advantageously retained for the insertion of one or more genes. Proteins which retain the enzymatic activity of the elongase means proteins with at least 10%, preferably 20%, especially preferably 30%, very especially preferably 40% of the original enzyme activity compared with the protein encoded by SEQ ID NO:2.

Homologs of SEQ ID NO:1 also means, for example, bacterial, fungal and plant homologs, truncated sequences, single-stranded DNA or RNA of the coding and noncoding DNA sequence.

Homologs of SEQ ID NO:1 also means derivatives such as, for example, promoter variants. The promoters upstream of the nucleotide sequences stated can be modified by one or more nucleotide substitutions, by insertion(s) and/or deletion(s), without, however, interfering with the functionality or activity of the promoters. It is furthermore possible for the activity of the promoters to be increased by modification of their sequence or for them to be replaced completely by more active promoters, even from heterologous organisms.

Moreover, the nucleic acid molecule according to the invention can only comprise part of the coding region of one of the sequences in SEQ ID NO:1, for example a fragment which can be used as probe or primer or a fragment which encodes a biologically active segment of a PSE. The nucleotide sequences identified by cloning the PSE gene of *P. infestans* allow the generation of probes and primers which are designed for identifying and/or cloning PSE homologs in other cell types and organisms and PSE homologs from other Oomycetes or related species. The probe/primer normally comprises essentially purified oligonucleotide. The oligonucleotide normally comprises a nucleotide sequence region which hybridizes under stringent conditions with at least approximately 12, preferably approximately 16, more preferably approximately 25, 40, 50 or 75 successive nucleotides of a sense strand of one of the sequences stated in SEQ ID NO:1, of an antisense strand of one of the sequences stated in SEQ ID NO:1, or its homologs, derivatives and analogs or naturally occurring mutants thereof. Primers based on a nucleotide sequence of SEQ ID NO:1 can be used in PCR reactions for cloning PSE homologs. Probes based on the PSE nucleotide sequences can be used for detecting transcripts or genomic sequences which encode the same or homologous proteins. In preferred embodiments, the probe additionally comprises a labeling group bound thereto, for example a radioisotope, a fluorescent compound, an enzyme or an enzyme cofactor. These probes can be used as part of a test kit for genomic markers for identifying cells which misexpress a PSE, for example by measuring an amount of a PSE-encoding nucleic acid in a cell sample, for example measuring the PSE mRNA level, or for determining whether a genomic PSE gene is mutated or deleted.

In one embodiment, the nucleic acid molecule according to the invention encodes a protein or a part thereof which comprises an amino acid sequence which has sufficient homology with an amino acid sequence of SEQ ID NO:2 for the protein or the part thereof to retain the ability to participate in the metabolism of compounds required for the synthesis of cell membranes in microorganisms or plants or in the transport of molecules via these membranes or in the fatty acid synthesis. As used in the present context, the term "sufficient homology" relates to proteins or parts thereof whose amino acid sequences have a minimum number of amino acid residues (for example an amino acid residue with a similar side chain, such as an amino acid residue in one of the sequences of SEQ ID NO:2) which are identical with or equivalent to an amino acid sequence of SEQ ID NO:2 so that the protein or the part thereof can participate in the metabolism of compounds required for the synthesis of cell membranes in microorganisms or plants or in the transport of molecules via these membranes. As described herein, protein components of these metabolic pathways for membrane components or membrane transport systems can play a role in the production and secretion of one or more fine chemicals. Examples of these activities are also described herein. Thus, the "function of a PSE" contributes either directly or indirectly to the yield, production and/or production efficiency of one or more fine chemicals. Examples of PSE substrate specificities of the catalytic activity are stated in Table I.

In a further embodiment, derivatives of the nucleic acid molecule according to the invention encode proteins with at least approximately 50 to 60%, preferably at least approximately 60 to 70% and more preferably at least approximately 70 to 80%, 80 to 90%, 90 to 95% and most preferably at least approximately 96%, 97%, 98%, 99% or more homology with a complete amino acid sequence of SEQ ID NO:2. The homology of the amino acid sequence was determined over the entire sequence region using the program PileUp (J. Mol. Evolution., 25, 351–360, 1987, Higgins et al., CABIOS, 5, 1989:151–153).

Parts of proteins encoded by the PSE nucleic acid molecules according to the invention are preferably biologically active parts of one of the PSEs. As used herein, the term "biologically active part of a PSE" is intended to comprise a segment, for example a domain/motif, of a PSE which can participate in the metabolism of compounds required for the synthesis of cell membranes in microorganisms or plants or in the transport of molecules via these membranes or which is involved in fatty acid synthesis or which has an activity stated in Table I. An assay of the enzymatic activity can be carried out in order to determine whether a PSE or a biologically active part thereof can participate in the metabolism of compounds required for the synthesis of cell membranes in microorganisms or plants or in the transport of molecules via these membranes. These assay methods as described in detail in Example 8 of the examples section are known to the skilled worker.

Additional nucleic acid fragments which encode biologically active segments of a PSE can be generated by isolating part of one of the sequences in SEQ ID NO:2, expressing the encoded segment of the PSE or of the peptide (for example by recombinant expression in vitro) and determining the activity of the encoded part of the PSE or of the peptide.

Moreover, the invention comprises nucleic acid molecules which differ from one of the nucleotide sequences shown in SEQ ID NO:1 (and parts thereof) owing to the degeneracy of the genetic code and which thus encode the same PSE as the one encoded by the nucleotide sequences shown in SEQ ID NO:1. In another embodiment, an isolated nucleic acid molecule according to the invention has a nucleotide sequence which encodes a protein with an amino acid sequence shown in SEQ ID NO:2. In a further embodiment, the nucleic acid molecule according to the invention encodes a full-length Phytophthora infestans protein which is essentially homologous with an amino acid sequence of SEQ ID NO:2 (which is encoded by an open reading frame shown in SEQ ID NO:1).

In addition to the *Phytophthora infestans* PSE nucleotide sequences shown in SEQ ID NO:1, the skilled worker recognizes that DNA sequence polymorphisms may exist which lead to changes in the amino acide sequences of the PSEs within a population (for example the *Phytophthora infestans* population). These genetic polymorphisms in the PSE gene can exist between individuals within a population owing to natural variation. As used in the present context, the term "gene" and "recombinant gene" refer to nucleic acid molecules with an open reading frame which encodes a PSE, preferably a Phytophthora infestans PSE. These natural variants usually cause a variance of 1 to 5% in the nucleotide sequence of the PSE gene. All of these nucleotide variations and resulting amino acid polymorphisms in PSE which are the result of natural variation and do not alter the functional activity of PSEs are intended to come within the scope of the invention.

Nucleic acid molecules which correspond to the natural variants and non-*Phytophthora infestans* homologs, -derivatives and -analogs of the *Phytophthora infestans* PSE cDNA according to the invention can be isolated in accordance with standard hybridization techniques under stringent hybridization conditions owing to their homology with the *Phytophthora infestans* PSE nucleic acid disclosed herein using the *Phytophthora infestans* cDNA or a part thereof as hybridization probe. In another embodiment, an isolated nucleic acid molecule according to the invention has a minimum length of 15 nucleotides and hybridizes under stringent conditions with the nucleic acid molecule which comprises a nucleotide sequence of SEQ ID NO:1. In other embodiments, the nucleic acid has a minimum length of 25, 50, 100, 250 or more nucleotides. The term "hybridizes under stringent conditions" as used in the present context is intended to describe hybridization and wash conditions under which nucleotide sequences which have at least 60% homology with each other usually remain hybridized with each other. The conditions are preferably such that sequences which have at least approximately 65%, more preferably at least approximately 70% and even more preferably at least approximately 75% or more homology with each other usually remain hybridized with each other. These stringent conditions are known to the skilled worker and can be found in Current Protocols in Molecular Biology, John Wiley & Sons, N.Y. (1989), 6.3.1–6.3.6. A preferred, non-limiting example of stringent hybridization conditions are hybridizations in 6× sodium chloride/sodium citrate (sodium chloride/sodium citrate=SSC) at approximately 45° C. followed by one or more wash steps in 0.2×SSC, 0.1% SDS at 50 to 65° C. It is known to the skilled worker that these hybridization conditions differ depending on the type of the nucleic acid and, for example when organic solvents are present, with regard to buffer temperature and concentration. For example, the temperature differs under "standard hybridization conditions" depending on the type of the nucleic acid between 42° C. and 58° C. in aqueous buffer with a concentration of 0.1 to 5×SSC (pH 7.2). If organic solvent is present in the abovementioned buffer, for example 50% formamide, the temperature under standard conditions is approximately 42° C. The hybridization conditions for DNA:DNA hybrids are preferably for example 0.1×SSC and 20° C. to 45° C., preferably between 30° C. and 45° C. The hybridization conditions for DNA:RNA hybrids are preferably for example 0.1×SSC and 30° C. to 55° C., preferably between 45° C. and 55° C. The abovementioned hybridization temperatures are determined for example for a nucleic acid approximately 100 bp (=base pairs) in length and a G+C content of 50% in the absence of formamide. The skilled worker knows how the hybridization conditions required can be determined with reference to textbooks, such as the one mentioned above or from the following textbooks: Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford. The skilled worker knows that the development type and time of the hybridization results influences the hybridization result. He is capable of optimizing, in simple experiments, the development conditions in such a way that the abovementioned hybridization gives reliable unambiguous results.

Preferably, an isolated nucleic acid molecule according to the invention which hybridizes under stringent conditions with a sequence of SEQ ID NO:1 corresponds to a naturally occurring nucleic acid molecule. As used in the present context, a "naturally occurring" nucleic acid molecule refers to an RNA or DNA molecule with a nucleotide sequence which occurs in nature (for example which encodes a natural protein). In one embodiment, the nucleic acid encodes a naturally occurring *Phytophthora infestans* PSE.

In addition to naturally occurring variants of the PSE sequence which may exist in the population, the skilled worker furthermore recognizes that changes by means of mutation may also be introduced into a nucleotide sequence of SEQ ID NO:1, which leads to changes in the amino acid sequence of the encoded PSE without adversely affecting the functionality of the PSE protein. For example, nucleotide substitutions which lead to amino acid substitutions on "nonessential" amino acid residues can be generated in a sequence of SEQ ID NO:1. A "nonessential" amino acid residue is a residue which can be altered in a wild-type sequence of one of the PSEs (SEQ ID NO:2) without altering the activity of the PSE, while an "essential" amino acid residue is required for the PSE activity. Other amino acid residues (for example those which are not conserved, or only semi-conserved, in the domain with PSE activity), however, may not be essential for the activity and can therefore probably be altered without altering the PSE activity.

Accordingly, a further aspect of the invention relates to nucleic acid molecules which encode PSEs comprising altered amino acid residues which are not essential for the PSE activity. These PSEs differ from a sequence in SEQ ID NO:2 with regard to the amino acid sequence while still retaining at least one of the PSE activities described herein. In one embodiment, the isolated nucleic acid molecule comprises a nucleotide sequence encoding a protein, the protein comprising an amino acid sequence with at least approximately 50% homology with an amino acid sequence of SEQ ID NO:2 and being able to participate in the metabolism of compounds required for the synthesis of cell membranes in *Phytophthora infestans* or in the transport of molecules via these membranes or being involved in the fatty acid metabolism or having one or more activities listed in Table I. The protein encoded by the nucleic acid molecule preferably has at least approximately 50 to 60% homology with one of the sequences in SEQ ID NO:2, more preferably at least approximately 60 to 70% homology with one of the sequences in SEQ ID NO:2, even more preferably at least approximately 70 to 80%, 80 to 90%, 90 to 95% homology with one of the sequences in SEQ ID NO:2, and most preferably at least approximately 96%, 97%, 98% or 99% homology with one of the sequences in SEQ ID NO:2.

To determine the percentage homology of two amino acid sequences (for example one of the sequences of SEQ ID NO:2 and a mutated form thereof) or of two nucleic acids, the sequences are written one underneath the other to allow optimal comparison (for example, gaps may be introduced into the sequence of a protein or of a nucleic acid in order to generate an optimal alignment with the other protein or the other nucleic acid). Then, the amino acid residues or nucleotides on the corresponding amino acid positions or nucleotide positions are compared. If a position in a sequence (for example one of the sequences of SEQ ID NO:2) is occupied by the same amino acid residue or the same nucleotide as the corresponding position in the other sequence (for example a mutated form of the sequence selected from SEQ ID NO:2), then the molecules are homologous at this position (i.e. amino acid or nucleic acid "homology" as used in the present context corresponds to amino acid or nucleic acid "identity"). The percentage homology between the two sequences is a function of the number of identical positions which the sequences share (i.e. % homology=number of identical positions/total number of positions×100).

An isolated nucleic acid molecule which encodes a PSE which is homologous with a protein sequence of SEQ ID NO:2 can be generated by introducing one or more nucleotide substitutions, additions or deletions into a nucleotide sequence of SEQ ID NO:1 so that one or more amino acid substitutions, additions or deletions are introduced into the encoded protein. Mutations can be introduced into one of the sequences of SEQ ID NO:1 by standard techniques, such as site-directed mutagenesis and PCR-mediated mutagenesis. Preferably, conservative amino acid substitutions are generated at one or more of the predicted nonessential amino acid residues. In a "conservative amino acid substitution", the amino acid residue is exchanged for an amino acid residue with a similar side chain. Families of amino acid residues with similar side chains have been defined in the specialist field. These families comprise amino acids with basic side chains (for example lysine, arginine, histidine), acidic side chains (for example aspartic acid, glutamic acid), uncharged polar side chains (for example glycine, asparagine, glutamine, serine, threonine, tyrosine, cysteine), unpolar side chains, (for example alanine, valine, leucine, isoleucine, proline, phenylalanine, methionine, tryptophan), beta-branched side chains (for example threonine, valine, isoleucine) and aromatic side chains (for example tyrosine, phenylalanine, tryptophan, histidine). A predicted nonessential amino acid residue in a PSE is thus preferably exchanged for another amino acid residue from the same side-chain family. As an alternative, in another embodiment, the mutations can be introduced randomly over all or part of the PSE-encoding sequence, for example by saturation mutagenesis, and the resulting mutants can be screened for the PSE activity described herein in order to identify mutants which retain PSE activity. After the mutagenesis of one of the sequences of SEQ ID NO:1, the encoded protein can be expressed recombinantly, and the activity of the protein can be determined, for example using the assay described herein (see examples section).

In addition to the nucleic acid molecules which encode the above-described PSEs, a further aspect of the invention relates to isolated nucleic acid molecules which are "antisense" thereto. An "antisense" nucleic acid comprises a nucleotide sequence which is complementary to a "sense" nucleic acid which encodes a protein, for example complementary to the coding strand of a double-stranded cDNA molecule or complementary to an mRNA sequence. Accordingly, an antisense nucleic acid can bind to a sense nucleic acid via hydrogen bonds. The antisense nucleic acid can be complementary to a complete PSE-encoding strand or only to part thereof. In one embodiment, an antisense nucleic acid molecule is "antisense" to a "coding region" of the coding strand of a nucleotide sequence encoding a PSE. The term "coding region" refers to the region of the nucleotide sequence which comprises codons which are translated into amino acid residues (for example the entire coding region which starts and ends with the stop codon, i.e. the last codon before the stop codon). In a further embodiment, the antisense nucleic acid molecule is "antisense" to a "noncoding region" of the coding strand of a nucleotide sequence encoding PSE. The term "noncoding region" refers to 5' and 3' sequences which flank the coding region and are not translated into amino acids (i.e. which are also termed 5'- and 3'-untranslated regions).

Taking into consideration the PSE-encoding sequences disclosed herein of the coding strand (for example the sequences shown in SEQ ID NO:1), antisense nucleic acids according to the invention can be designed in accordance with the rules of the Watson-Crick base pairing. The antisense nucleic acid molecule can be complementary to all of the coding region of PSE mRNA, but is more preferably an oligonucleotide which is "antisense" to only part of the coding or noncoding region of PSE mRNA. For example, the antisense oligonucleotide can be complementary to the region around the translation start position of PSE mRNA. An antisense oligonucleotide can have a length of, for example, approximately 5, 10, 15, 20, 25, 30, 35, 40, 45 or 50 and more nucleotides. An antisense nucleic acid according to the invention can be constructed by processes known in the art using chemical synthesis and enzymatic ligation reactions. For example, an antisense nucleic acid (for example an antisense oligonucleotide) can be synthesized chemically, making use of naturally occurring nucleotides or variously modified nucleotides which are such that they increase the biological stability of the molecules or increase the physical stability of the duplex formed between the antisense and the sense nucleic acid; for example, phosphorothioate derivatives and acridin-substituted nucleotides may be used. Examples of modified nucleotides which may be used for generating the antisense nucleic acid are, inter alia, 5-fluorouracil, 5-bromouracil, 5-chlorouracil, 5-iodouracil, hypoxanthin, xanthin, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, methyl uracil-5-oxyacetate, uracil-5-oxyacetic acid (v), 5-methyl-2-thiouracil, 3-(3-amino-3-N-2-carboxypropyl)uracil, (acp3)w and 2,6-diaminopurine. Alternatively, the antisense nucleic acid can be generated biologically using an expression vector to which a nucleic acid has been subcloned in antisense orientation (i.e. RNA which is transcribed by the nucleic acid introduced is in antisense orientation relative to a target nucleic acid of interest, which is described in greater detail in the subsection which follows).

The antisense nucleic acid molecules according to the invention are usually administered to a cell or generated in situ so that they hybridize with, or bind to, the cellular mRNA and/or the genomic DNA encoding a PSE, thus inhibiting expression of the protein, for example by inhibiting transcription and/or translation. Hybridization can be effected by conventional nucleotide complementarity with formation of a stable duplex or, for example in the case of an antisense nucleic acid molecule which binds DNA duplices, by specific interactions in the large cleft of the double helix. The antisense molecule can be modified in such a manner that it specifically binds to a receptor or to an antigen expressed at a selected cell surface, for example by binding the antisense nucleic acid molecule to a peptide or an antibody, each of which binds to a cell surface receptor or an antigen. The cells can also be provided with the antisense nucleic acid molecule using the vectors described herein. Vector constructs in which the antisense nucleic acid molecule is under the control of a strong prokaryotic, viral or eukaryotic promoter, inclusive of a plant promoter, are preferred for achieving sufficient intracellular concentrations of the antisense molecules.

In a further embodiment, the antisense nucleic acid molecule according to the invention is an α-anomeric nucleic acid molecule. An α-anomeric nucleic acid molecule forms specific double-stranded hybrids with complementary RNA, the strands running parallel to each other, in contrast to ordinary β-units [Gaultier et al. (1987) Nucleic Acids Res. 15:6625–6641]. Moreover, the antisense nucleic acid molecule can comprise a 2'-o-methylribonucleotide [Inoue et al. (1987) Nucleic Acids Res. 15:6131–6148] or a chimeric RNA-DNA analog [Inoue et al. (1987) FEBS Lett. 215: 327–330].

In a further embodiment, an antisense nucleic acid according to the invention is a ribozyme. Ribozymes are catalytic RNA molecules with ribonuclease activity which can cleave a single-stranded nucleic acid, such as an mRNA, to which they have a complementary region. Thus, ribozymes, for example hammerhead ribozymes (described in Haselhoff and Gerlach (1988) Nature 334:585–591), can be used for the catalytic cleavage of PSE mRNA transcripts in order to inhibit the translation of PSE mRNA. A ribozyme with specificity for a PSE-encoding nucleic acid can be designed on the basis of the nucleotide sequence of a PSE cDNA disclosed herein (i.e. 38_Ck21_g07fwd in SEQ ID NO:1) or on the basis of a heterologous sequence to be isolated in accordance with the processes taught in the present invention. For example, a derivative of a Tetrahymena-L-19-IVS RNA can be constructed, in which the nucleotide sequence of the active site is complementary to the nucleotide sequence to be cleaved in PSE-encoding mRNA. See, for example, Cech et al., U.S. Pat. No. 4,987,071 and Cech et al., U.S. Pat. No. 5,116,742. As an alternative, PSE mRNA can be used for selecting a catalytic RNA with a specific ribonuclease activity from amongst a pool of RNA molecules (see, for example, Bartel, D., and Szostak, J. W. (1993) Science 261:1411–1418).

As an alternative, PSE gene expression can be inhibited by directing nucleotide sequences which are complementary to the regulatory region of a PSE nucleotide sequence (for example a PSE promoter and/or enhancer) in such a way that triple helix structures are formed, which inhibit the transcription of a PSE gene in target cells (see generally Helene, C. (1991) Anticancer Drug Res. 6(6) 569–84; Helene, C., et al. (1992) Ann. N.Y. Acad. Sci. 660:27–36; and Maher. L. J. (1992) Bioassays 14(12):807–815).

As a further alternative, the PSE gene expression can be inhibited by cosuppression; a simultaneous expression of a combined antisense/sense strand (RNAi technique) is also advantageously possible.

B. Gene Construct

A further embodiment of the invention is a novel gene construct, which means an isolated nucleic acid derived from a plant or a fungus and encoding a polypeptide which elongates $C_{16}$- and/or $C_{18}$-fatty acids with at least two double bonds in the fatty acid by at least two carbon atoms, or the gene sequence of SEQ ID NO:1, its homologs, derivatives or analogs which are functionally linked to one or more regulatory signals, advantageously for increasing gene expression. Examples of these regulatory sequences are sequences which bind to inductors or repressors, and in this manner regulate the expression of the nucleic acid. In addition to these novel regulatory sequences, the natural regulation of these sequences before the actual structural genes may still be present and, if appropriate, have been genetically modified, so that the natural regulation has been switched off and the expression of the genes has been enhanced. However, the gene construct may also have a simpler structure, i.e. no additional regulatory signals have been inserted before the sequence SEQ ID NO:1 or their homologs and the natural promoter with its regulation has not been deleted. Instead, the natural regulatory sequence has been mutated in such a way that regulation no longer takes place and gene expression is enhanced. The gene construct may furthermore advantageously comprise one or more so-called enhancer sequences which are functionally linked to the promoter and which allow increased expression of the nucleic acid sequence. It is also possible additionally to insert advantageous sequences at the 3' end of the DNA sequences, for example further regulatory elements or terminators. The elongase genes may be present in one or more copies in the gene construct. It is advantageous for the insertion of further genes into organisms if further genes are present in the gene construct.

Advantageous regulation sequences for the novel process exist, for example, in promoters such as the cos, tac, trp, tet, trp-tet, lpp, lac, lpp-lac, lacIq, T7, T5, T3, gal, trc, ara, SP6, $\lambda$-$P_R$ or $\lambda$-$P_L$ promoter and are advantageously used in Gram-negative bacteria. Further advantageous regulatory sequences exist, for example, in Gram-positive promoters amy and SPO2, in the yeast or fungal promoters ADC1, MFα, AC, P-60, CYC1, GAPDH, TEF, rp28, ADH or in the plant promoters CaMV 35S [Franck et al., Cell 21 (1980) 285–294], PRP1 [Ward et al., Plant. Mol. Biol. 22 (1993)], SSU, OCS, lib4, usp, STLS1, B33, nos or in the ubiquitin or phaseolin promoter. Advantageous in this context are also inducible promoters, such as the promoters described in EP-A-0 388 186 (benzylsulfonamide-inducible), Plant J. 2, 1992:397–404 (Gatz et al., tetracyclin-inducible), EP-A-0 335 528 (abscisic acid-inducible) or WO 93/21334 (ethanol- or cyclohexenol-inducible). Other suitable plant promoters are the cytosolic FBPase or the potato ST-LSI promoter (Stockhaus et al., EMBO J. 8, 1989, 2445), the Glycine max phosphoribosylpyrophosphate amidotransferase promoter (Genbank Accession No. U87999) or the node-specific promoter described in EP-A-0 249 676. Especially advantageous promoters are promoters which allow expression in tissues which are involved in fatty acid biosynthesis. Very especially advantageous are seed-specific promoters, such as the usp, the LEB4, the phaseolin or the napin promoter. Further especially advantageous promoters are seed-specific promoters which can be used for monocots or dicots which are described in U.S. Pat. No. 5,608,152 (oilseed rape napin promoter), WO 98/45461 (*Arobidopsis* phaseolin promoter), U.S. Pat. No. 5,504,200 (*Phaseolus vulgaris* phaseolin promoter), WO 91/13980 (*Brassica* Bce4-promoter), Baeumlein et al., Plant J., 2, 2, 1992:233–239 (leguminous LEB4 promoter), these promoters being suitable for dicots. The following promoters are suitable, for example, for monocots: the barley lpt-2 or lpt-1 promoter (WO 95/15389 and WO 95/23230), the hordein promoter, and other suitable promoters described in WO 99/16890.

In principle, it is possible to use all natural promoters with their regulatory sequences, such as those mentioned above, for the novel process. It is also possible and advantageous additionally to use synthetic promoters.

As described above, the gene construct can also comprise further genes which are to be introduced into the organisms. It is possible and advantageous to introduce into the host organisms, and to express therein, regulatory genes such as genes for inductors, repressors or enzymes which, owing to their enzymatic activity, engage in the regulation of one or more genes of a biosynthetic pathway. These genes can be of heterologous or homologous origin. The inserted genes can have their own promoter or else be under the control of the promoter of sequence SEQ ID NO:1 or its homologs.

To express the other genes which are present, the gene construct advantageously comprises further 3'- and/or 5'-terminal regulatory sequences for enhancing expression, and these are selected for optimal expression as a function of the host organism chosen and the gene(s).

As mentioned above, these regulatory sequences are intended to make possible the specific expression of the genes and protein expression. Depending on the host organism, this may mean, for example, that the gene is expressed or overexpressed only after induction, or that it is expressed and/or overexpressed immediately.

Moreover, the regulatory sequences or regulatory factors can preferably have an advantageous effect on the expression of the genes which have been introduced, thus enhancing it. In this manner, it is possible that the regulatory elements are advantageously enhanced at the transcriptional level, using strong transcription signals, such as promoters and/or enhancers. However, it is furthermore also possible to enhance translation, for example by improving mRNA stability.

C. Recombinant Expression Vectors and Host Cells

A further aspect of the invention relates to vectors, preferably expression vectors comprising a nucleic acid which encode a PSE (or part thereof). As used in the present context, the term "vector" refers to a nucleic acid molecule which can transport another nucleic acid to which it is bound. One type of vector is a "plasmid", which represents a circular double-stranded DNA loop into which additional DNA segments can be ligated. A further type of vector is a viral vector, it being possible for additional DNA segments to be ligated into the viral genome. Certain vectors are capable of autonomous replication in a host cell into which they have been introduced (for example bacterial vectors with bacterial origin of replication and episomal mammalian vectors). Other vectors (for example nonepisomal mammalian vectors) are integrated into the genome of a host cell upon introduction into the host cell and so replicate together with the host genome. In addition, certain vectors can govern the expression of genes to which they are functionally linked. These vectors are referred to as "expression vectors" herein. Usually, expression vectors which are suitable for recombinant DNA techniques take the form of plasmids. In the present description, "plasmid" and "vector" may be used interchangeably since the plasmid is the most frequently used form of a vector. However, the invention is intended to comprise these other forms of expression vectors, such as viral vectors (for example replication-deficient retroviruses, adenoviruses and adeno-related viruses) which exert similar functions. Furthermore, the term vector is also intended to comprise other vectors known to the skilled worker, such as phages, viruses such as SV40, CMV, baculovirus, adenovirus, transposons, IS elements, phasmids, phagemids, cosmids, linear or circular DNA.

The recombinant expression vectors according to the invention comprise a nucleic acid according to the invention or a gene construct according to the invention in a form which is suitable for expressing the nucleic acid in a host cell, which means that the recombinant expression vectors comprise one or more regulatory sequences, selected on the basis of the host cells to be used for expression, which is or are functionally linked to the nucleic acid sequence to be expressed. In a recombinant expression vector, "functionally linked" means that the nucleotide sequence of interest is bound to the regulatory sequence(s) in such a way that expression of the nucleotide sequence is possible and they are bound to each other so that both sequences fulfill the predicted function which has been ascribed to the sequence (for example in an in-vitro transcription/translation system or in a host cell, when the vector is introduced into the host cell). The term "regulatory sequence" is intended to comprise promoters, enhancers and other expression control elements (for example polyadenylation signals). These regulatory sequences are described, for example, in Goeddel: Gene Expression Technology: Methods in Enzymology 185, Academic Press, San Diego, Calif. (1990), or see: Gruber and Crosby, in: Methods in Plant Molecular Biology and Biotechnology, CRC Press, Boca Raton, Fla., Ed.: Glick and Thompson, Chapter 7, 89–108, including the references therein. Regulatory sequences comprise those which control the constitutive expression of a nucleotide sequence in many types of host cell and those which control the direct expression of the nucleotide sequence only in certain host cells under certain conditions. The skilled worker knows that the design of the expression vector may depend on factors such as the choice of the host cell to be transformed, the extent to which the desired protein is expressed, and the like. The expression vectors according to the invention can be introduced into host cells in order to produce proteins or peptides, including fusion proteins or fusion peptides, which are encoded by the nucleic acids as described herein (for example PSEs, mutant forms of PSEs, fusion proteins and the like).

The recombinant expression vectors according to the invention can be designed for expressing PSEs in prokaryotic or eukaryotic cells. For example, PSE genes can be expressed in bacterial cells, such as *C. glutamicum*, insect cells (using baculovirus expression vectors), yeast and other fungal cells (see Romanos, M. A., et al. (1992) "Foreign gene expression in yeast: a review", Yeast 8:423–488; van den Hondel, C. A. M. J. J., et al. (1991) "Heterologous gene expression in filamentous fungi", in: More Gene Manipulations in Fungi, J. W. Bennet & L. L. Lasure, Ed., pp. 396–428: Academic Press: San Diego; and van den Hondel, C. A. M. J. J., & Punt, P. J. (1991) "Gene transfer systems and vector development for filamentous fungi, in: Applied Molecular Genetics of Fungi, Peberdy, J. F., et al., Ed., pp. 1–28, Cambridge University Press: Cambridge), algae (Falciatore et al., 1999, Marine Biotechnology. 1, 3:239–251), ciliates of the following types: *Holotrichia, Peritrichia, Spirotrichia, Suctoria, Tetrahymena, Paramecium, Colpidium, Glaucoma, Platyophrya, Potomacus, Pseudocohnilembus, Euplotes, Engelmaniella* and *Stylonychia*, in particular of the genus *Stylonychia lemnae*, using vectors and following a transformation method as described in WO 98/01572, and cells of multicelled plants (see Schmidt, R. and Willmitzer, L. (1988) "High efficiency *Agrobacterium tumefaciens*-mediated transformation of *Arabidopsis thaliana* leaf and cotyledon explants" Plant Cell Rep.:583–586; Plant Molecular Biology and Biotechnology, C Press, Boca Raton, Fla., Chapter 6/7, pp.71–119 (1993); F. F. White, B. Jenes et al., Techniques for Gene Transfer, in: Transgenic Plants, Vol. 1, Engineering and Utilization, Ed.: Kung and R. Wu, Academic Press (1993), 128–43; Potrykus, Annu. Rev. Plant Physiol. Plant Molec. Biol. 42 (1991), 205–225 (and references cited therein)) or nonhuman mammalian cells. Suitable host cells are furthermore discussed in Goeddel, Gene Expression Technology: Methods in Enzymology 185, Academic Press, San Diego, Calif. (1990). As an alternative, the recombinant expression vector can be transcribed and translated in vitro, for example using T7 promoter regulatory sequences and T7 polymerase.

In prokaryotes, proteins are usually expressed with vectors containing constitutive or inducible promoters which control the expression of fusion proteins or nonfusion proteins. Fusion vectors add a series of amino acids to a protein encoded therein, usually at the amino terminus of the recombinant protein, but also at the C terminus or fused within suitable regions in the proteins. These fusion vectors usually have three tasks: 1) to enhance the expression of recombinant protein; 2) to increase the solubility of the recombinant protein and 3) to support the purification of the recombinant protein by acting as ligand in affinity purification. In the case of fusion expression vectors, a proteolytic cleavage site is frequently introduced at the site where the fusion unit and the recombinant protein are linked, so that the recombinant protein can be separated from the fusion unit after purification of the fusion protein. These enzymes and their corresponding recognition sequences comprise factor Xa, thrombin and enterokinase.

Typical fusion expression vectors are, inter alia, pGEX (Pharmacia Biotech Inc; Smith, D. B., and Johnson, K. S. (1988) Gene 67:31–40), pMAL (New England Biolabs, Beverly, Mass.) and pRIT5 (Pharmacia, Piscataway, N.J.), where glutathione S-transferase (GST), maltose-E-binding protein or protein A is fused to the recombinant target protein. In one embodiment, the PSE-encoding sequence is cloned into a pGEX expression vector to generate a vector encoding a fusion protein which comprises, from the N terminus to the C terminus, GST-thrombin cleavage site-X-protein. The fusion protein can be purified by affinity chromatography using glutathione-agarose resin. Recombinant PSE which is not fused with GST can be obtained by cleaving the fusion protein with thrombin.

Examples of suitable inducible nonfusion E. coli expression vectors are, inter alia, pTrc (Amann et al. (1988) Gene 69:301–315) and pET 11d (Studier et al., Gene Expression Technology: Methods in Enzymology 185, Academic Press, San Diego, Calif. (1990) 60–89). Target gene expression of the pTrc vector is based on transcription by host RNA polymerase from a hybrid trp-lac fusion promoter. Target gene expression from the pET 11d vector is based on transcription from a T7-φ10-lac fusion promoter which is mediated by a coexpressed viral RNA polymerase (T7 gn1). This viral polymerase is provided by the host strains BL21 (DE3) or HMS174 (DE3) by a resident λ prophage which harbors a T7 φ1 gene under the transcriptional control of the lacUV 5 promoter.

Other vectors which are suitable for use in prokaryotic organisms are known to the skilled worker; these vectors are, for example, in E. coli pLG338, pACYC184, the pBR series such as pBR322, the pUC series such as pUC18 or pUC19, the M113mp series, pKC30, pRep4, pHS1, pHS2, pPLc236, pMBL24, pLG200, pUR290, pIN-III[113]-B1, ?gt11 or pBdCI, in Streptomyces pIJ101, pIJ364, pIJ702 or pIJ361, in Bacillus pUB110, pC194 or pBD214, in Corynebacterium pSA77 or pAJ667.

A strategy of maximizing the expression of recombinant protein is to express the protein in a host bacterium whose ability to cleave the recombinant protein proteolytically is disrupted (Gottesman, S., Gene Expression Technology: Methods in Enzymology 185, Academic Press, San Diego, Calif. (1990) 119–128). A further strategy is to modify the nucleic acid sequence of the nucleic acid to be inserted into an expression vector, so that the individual codons for each amino acid are those which are preferentially used in a bacterium selected for expression, such as C. glutamicum (Wada et al. (1992) Nucleic Acids Res. 20:2111–2118). Modification of these nucleic acid sequences according to the invention is carried out by standard techniques of DNA synthesis.

In a further embodiment, the PSE expression vector is a yeast expression vector. Examples of vectors for expression in the yeast S. cerevisiae include pYepSec1 (Baldari et al. (1987) Embo J. 6:229–234), pMFa (Kurjan and Herskowitz (1982) Cell 30:933–943), pJRY88 (Schultz et al. (1987) Gene 54:113–123) and pYES2 (Invitrogen Corporation, San Diego, Calif.). Vectors and methods for the construction of vectors which are suitable for use in other fungi, such as the filamentous fungi, include those which are described in detail in: van den Hondel, C. A. M. J. J., & Punt, P. J. (1991) "Gene transfer systems and vector development for filamentous fungi, in: Applied Molecular Genetics of fungi, J. F. Peberdy et al., Ed., pp. 1–28, Cambridge University Press: Cambridge, or in: More Gene Manipulations in Fungi [J. W. Bennet & L. L. Lasure, Ed., pp. 396–428: Academic Press: San Diego]. Further suitable yeast vectors are, for example, 2∝M, pAG-1, YEp6, YEp13 or pEMBLYe23.

As an alternative, the PSEs according to the invention can be expressed in insect cells using baculovirus expression vectors. Baculovirus vectors which are available for expressing proteins in cultured insect cells (for example Sf9 cells) include the pAc series (Smith et al. (1983) Mol. Cell Biol. 3:2156–2165) and the pVL series (Lucklow and Summers (1989) Virology 170:31–39).

The abovementioned vectors are just a short review of suitable vectors which are possible. Further plasmids are known to the skilled worker and are described, for example, in: Cloning Vectors (Ed. Pouwels, P. H., et al., Elsevier, Amsterdam-New York-Oxford, 1985, ISBN 0 444 904018).

In yet a further embodiment, a nucleic acid according to the invention is expressed in mammalian cells using a mammalian expression vector. Examples of mammalian expression vectors include pCDM8 (Seed, B. (1987) Nature 329:840) and pMT2PC (Kaufman et al. (1987) EMBO J. 6:187–195). When used in mammalian cells, the control functions of the expression vector are frequently provided by viral regulatory elements. Promoters which are usually used are derived, for example, from polyoma, adenovirus2, cytomegalovirus and simian virus 40. Other suitable expression systems for prokaryotic and eukaryotic cells can be found in Chapters 16 and 17 of Sambrook, J., Fritsch, E. F., and Maniatis, T., Molecular Cloning: A Laboratory Manual, 2nd Edition, Cold Spring Harbor Laboratory, Cold Spring Harbor Laboratory Press, Cold Spring Harbor, N.Y., 1989.

In another embodiment, the recombinant mammalian expression vector can control the expression of the nucleic acid preferably in a specific cell type (for example, tissue-specific regulatory elements are used for expressing the nucleic acid). Tissue-specific regulatory elements are known in the art. Nonlimiting examples of suitable tissue-specific promoters are, inter alia, the albumin promoter (liver-specific; Pinkert et al. (1987) Genes Dev. 1:268–277), lymphoid-specific promoters (Calame and Eaton (1988) Adv. Immunol. 43:235–275), in particular promoters of T-cell receptors (Winoto and Baltimore (1989) EMBO J. 8:729–733) and immunoglobulins (Banerji et al. (1983) Cell 33:729–740; Queen and Baltimore (1983) Cell 33:741–748), neuron-specific promoters (for example neurofilament promoter; Byrne and Ruddle (1989) PNAS 86:5473–5477), pancreas-specific promoters (Edlund et al., (1985) Science 230:912–916) and mamma-specific promoters (for example milk serum promoter; U.S. Pat. No. 4,873,316 and European Patent Application Publication No. 264 166). Also included are development-regulated promoters, for example the mouse hox promoters (Kessel and Gruss (1990) Science 249:374–379) and the fetoprotein promoter (Campes and Tilghman (1989) Genes Dev. 3:537–546).

In a further embodiment, the PSEs according to the invention can be expressed in single-celled plant cells (such as algae), see Falciatore et al., 1999, Marine Biotechnology 1 (3):239–251 and references cited therein, and in plant cells from higher plants (for example spermatophytes such as crops). Examples of plant expression vectors include those which are described in detail in: Becker, D., Kemper, E., Schell, J., and Masterson, R. (1992) "New plant binary vectors with selectable markers located proximal to the left border", Plant Mol. Biol. 20:1195–1197; and Bevan, M. W. (1984) "Binary *Agrobacterium* vectors for plant transformation", Nucl. Acids Res. 12:8711–8721; Vectors for Gene Transfer in Higher Plants; in: Transgenic Plants, Vol. 1, Engineering and Utilization, Ed.: Kung and R. Wu, Academic Press, 1993, pp. 15–38.

A plant expression cassette preferably comprises regulatory sequences which can control gene expression in plant cells and which are functionally linked, so that each sequence can fulfill its function, such as transcriptional termination, for example polyadenylation signals. Preferred polyadenylation signals are those derived from *Agrobacterium tumefaciens* t-DNA, such as gene 3 of the Ti plasmid pTiACH5, which is known as octopine synthase (Gielen et al., EMBO J. 3 (1984) 835 et seq.) or functional equivalents thereof, but all other terminators which are functionally active in plants are also suitable.

Since plant gene expression is very frequently not limited to the transcriptional level, a plant expression cassette preferably comprises other functionally linked sequences, such as translation enhancers, for example the overdrive sequence, which contains the 5'-untranslated tobacco mosaic virus leader sequence, which increases the protein/RNA ratio (Gallie et al., 1987, Nucl. Acids Research 15:8693–8711).

Plant gene expression must be functionally linked to a suitable promoter which effects gene expression in a cell- or tissue-specific manner with the correct timing. Preferred promoters are those which lead to constitutive expression (Benfey et al., EMBO J. 8 (1989) 2195–2202), such as those which are derived from plant viruses such as 35S CAMV (Franck et al., Cell 21 (1980) 285–294), 19S CaMV (see also U.S. Pat. No. 5,352,605 and WO 84/02913) or plant promoters such as the Rubisco small subunit promoter described in U.S. Pat. No. 4,962,028.

Other sequences which are preferred for use for functional linkage in plant gene expression cassettes are targeting sequences, which are required for targeting the gene product in its corresponding cell compartment (for a review, see Kermode, Crit. Rev. Plant Sci. 15, 4 (1996) 285–423 and references cited therein), for example into the vacuole, the nucleus, all types of plastids such as amyloplasts, chloroplasts, chromoplasts, the extracellular space, the mitochondria, the endoplasmic reticulum, elaioplasts, peroxisomes and other compartments of plant cells.

Plant gene expression can also be facilitated via a chemically inducible promoter (for a review, see Gatz 1997, Annu. Rev. Plant Physiol. Plant Mol. Biol., 48:89–108). Chemically inducible promoters are particularly suitable when it is desired for gene expression to take place in a specific manner with regard to timing. Examples of such promoters are a salicylic acid-inducible promoter (WO 95/19443), a tetracyclin-inducible promoter (Gatz et al. (1992) Plant J. 2, 397–404) and an ethanol-inducible promoter.

Other suitable promoters are promoters which respond to biotic or abiotic stress conditions, for example the pathogen-induced PRP1 gene promoter (Ward et al., Plant. Mol. Biol. 22 (1993) 361–366), the heat-inducible tomato hsp80 promoter (U.S. Pat. No. 5,187,267), the low-temperature-inducible potato alpha-amylase promoter (WO 96/12814) or the wound-inducible pinII promoter (EP-A-0 375 091).

Promoters which are particularly preferred are those which lead to gene expression in tissues and organs in which lipid and oil biosynthesis take place, in seed cells such as endosperm cells and cells of the developing embryo. Promoters which are suitable are the oilseed rape napin gene promoter (U.S. Pat. No. 5,608,152), the *Vicia faba* USP promoter (Baeumlein et al., Mol Gen Genet, 1991, 225 (3):459–67), the Arabidopsis oleosin promoter (WO 98/45461), the Phaseolus vulgaris phaseolin promoter (U.S. Pat. No. 5,504,200), the *Brassica* Bce4 promoter (WO 91/13980) or the legumin B4 promoter (LeB4; Baeumlein et al., 1992, Plant Journal, 2 (2):233–9), and promoters which lead to the seed-specific expression in monocots such as maize, barley, wheat, rye, rice and the like. Notable promoters which are suitable are the barley lpt2 or lpt1 gene promoter (WO 95/15389 and WO 95/23230), or the promoters described in WO 99/16890 (promoters from the barley hordein gene, the rice glutelin gene, the rice oryzin gene, the rice prolamin gene, the wheat gliadin gene, the wheat glutelin gene, the maize zein gene, the oat glutelin gene, the sorghum kasirin gene, and the rye secalin gene).

Promoters which are also particularly suitable are those which lead to plastid-specific expression, since plastids are the compartment in which the precursors and some end products of lipid biosynthesis are synthesized. Suitable promoters such as the viral RNA polymerase promoter are described in WO 95/16783 and WO 97/06250, and the Arabidopsis clpP promoter, described in WO 99/46394.

The invention furthermore provides a recombinant expression vector comprising a DNA molecule according to the invention which is cloned into the expression vector in antisense orientation, i.e. the DNA molecule is functionally linked to a regulatory sequence in such a way that it allows the expression (by transcribing the DNA molecule) of an RNA molecule which is "antisense" to the PSE mRNA. Regulatory sequences may be selected which are functionally linked to a nucleic acid cloned in antisense orientation and which control the continuous expression of the antisense RNA molecule in a multiplicity of cell types, for example, viral promoters and/or enhancers or regulatory sequences may be selected which control the constitutive, tissue-specific or cell type-specific expression of antisense RNA. The antisense expression vector may be present in the form of a recombinant plasmid, phagemid or attenuated virus in which the antisense nucleic acids are produced under the control of a highly effective regulatory region whose activity can be determined by the cell type into which the vector has been introduced. For an explanation of the regulation of gene expression by means of antisense genes, see Weintraub, H., et al., Antisense-RNA as a molecular tool for genetic analysis, Reviews—Trends in Genetics, Vol. 1(1) 1986.

A further aspect of the invention relates to host cells into which a recombinant expression vector according to the invention has been introduced. The terms "host cell", "recombinant host cell" and "transgenic host cell" are used interchangeably in the present context. Naturally, these terms do not only refer to the particular target cell, but also to the progeny or potential progeny of this cell. Since specific modifications may occur in subsequent generations owing to mutation or environmental effects, this progeny is not necessarily identical with the parental cell, but is still comprehended by the scope of the term as used herein.

A host cell may be a prokaryotic or eukaryotic cell. For example, a PSE can be expressed in bacterial cells such as *C. glutamicum*, insect cells, fungal cells or mammalian cells (such as Chinese hamster ovary cells (CHO) or COS cells), algae, ciliates, plant cells, fungi or other microorganisms, such as *C. glutamicum*. Other suitable host cells are known to the skilled worker.

Vector DNA can be introduced into prokaryotic or eukaryotic cells via conventional transformation or transfection techniques. The terms "transformation" and "transfection", conjugation and transduction as used in the present context are intended to comprise a multiplicity of methods known in the art for introducing foreign nucleic acid (for example DNA) into a host cell, including calcium phosphate or calcium chloride coprecipitation, DEAE-dextran-mediated transfection, lipofection, natural competence, chemically mediated transfer, electroporation or particle bombardment. Suitable methods for the transformation or transfection of host cells, including plant cells, can be found in Sambrook et al. (Molecular Cloning: A Laboratory Manual, 2nd Ed., Cold Spring Harbor Laboratory, Cold Spring Harbor Laboratory Press, Cold Spring Harbor, N.Y., 1989) and other laboratory textbooks, such as Methods in Molecular Biology, 1995, Vol. 44, *Agrobacterium* protocols, Ed.: Gartland and Davey, Humana Press, Totowa, N.J.

It is known about the stable transfection of mammalian cells that only a minority of the cells integrate the foreign DNA into their genome, depending on the expression vector used and the transfection technique used. To identify and select these integrants, a gene which encodes a selectable marker (for example resistance to antibiotics) is usually introduced into the host cells together with the gene of interest. Preferred selectable markers comprise those which impart resistance to drugs such as G418, hygromycin and methotrexate, or, in plants, those which impart resistance to a herbicide such as glyphosphate or glufosinate. Further suitable markers are, for example, markers which encode genes which are involved in the biosynthesis pathways of, for example, sugars or amino acids, such as β-galactosidase, ura3 or ilv2. Markers which encode genes such as luciferase, gfp or other fluorescence genes are also suitable. These markers can be used in mutants in which these genes are not functional since they have been deleted for example by means of conventional methods. Furthermore, markers which encode a nucleic acid which encodes a selectable marker can be introduced into a host cell on the same vector as the one which encodes a PSE, or can be introduced on a separate vector. Cells which have been transfected stably with the nucleic acid introduced can be identified for example by drug selection (for example, cells which have the selectable marker integrated survive, whereas other cells die).

To generate a homologously recombinant microorganism, a vector is generated which contains at least one segment of a PSE gene into which a deletion, addition or substitution has been introduced in order to modify the PSE gene hereby, for example to functionally disrupt it. This PSE gene is preferably a *Physcomitrella patens* or *Phytophthora infestans* PSE gene, but a homolog or analog from other organisms, even from a mammalian, fungal or insect source, can also be used. In a preferred embodiment, the vector is designed in such a way that the endogenous PSE gene is functionally disrupted (i.e. no longer encodes a functional protein, also termed knock-out vector) upon homologous recombination. As an alternative, the vector can be designed such that the endogenous PSE gene mutates or is modified otherwise upon homologous recombination while still encoding a functional protein (for example, the upstream regulatory region can be modified in such a way that this leads to a modification of the expression of the endogenous PSE). To generate a point mutation via homologous recombination, DNA-RNA hybrids, which are also known as chimeraplasty and which are known from Cole-Strauss et al., 1999, Nucleic Acids Research 27(5):1323–1330 and Kmiec, Gene therapy, 1999, American Scientist, 87(3): 240–247 can also be used.

In the vector for homologous recombination, the modified segment of the PSE gene is flanked at its 5' and 3' end by additional nucleic acid of the PSE gene, so that homologous recombination is possible between the exogenous PSE gene which is present on the vector and an endogenous PSE gene in a microorganism or a plant. The additional flanking PSE nucleic acid is sufficiently long for successful homologous recombination with the endogenous gene. Usually, several hundred base pairs up to kilobases of flanking DNA (both on the 5' and on the 3' end) are present in the vector (for a description of vectors for homologous recombination, see, for example, Thomas, K. R., and Capecchi, M. R. (1987) Cell 51:503 or for the recombination in *Physcomitrella patens* on cDNA basis, see Strepp et al., 1998, Proc. Natl. Acad. Sci. USA 95 (8):4368–4373). The vector is introduced into a microorganism or plant cell (for example by means of polyethylene glycol-mediated DNA), and cells in which the PSE gene introduced has undergone homologous recombination with the endogenous PSE gene are selected using techniques known in the art.

In another embodiment, recombinant organisms such as microorganisms can be generated which contain selected systems which allow regulated expression of the gene introduced. The inclusion of a PSE gene in a vector, where it is placed under the control of the lac-operon, allows, for example, expression of the PSE gene only in the presence of IPTG. These regulatory systems are known in the art.

A host cell according to the invention, such as prokaryotic or eukaryotic host cells, growing either in culture or in a field, can be used for producing (i.e. expressing) a PSE. In plants, an alternative method can additionally be used by directly transferring DNA into developing flowers via electroporation or *Agrobacterium*-mediated gene transfer. Accordingly, the invention furthermore provides methods of producing PSEs using the host cells according to the invention. In one embodiment, the method comprises growing the host cell according to the invention (into which a recombinant expression vector encoding a PSE has been introduced or into whose genome a gene encoding a wild-type or modified PSE has been introduced) in a suitable medium until the PSE has been produced. In a further embodiment, the method comprises isolating the PSEs from the medium or the host cell.

Host cells which are suitable in principle for taking up the nucleic acid according to the invention, the novel gene product according to the invention or the vector according to the invention are all prokaryotic or eukaryotic organisms. The host organisms which are used advantageously are organisms such as bacteria, fungi, yeasts, nonhuman animal cells or plant cells. Further advantageous organisms are nonhuman animals or, preferably, plants or parts thereof. Fungi, yeasts or plants are preferably used, especially preferably fungi or plants, very especially preferably plants such as oil crops which contain large amounts of lipid compounds, such as oilseed rape, evening primrose, canola, peanut, linseed, soybean, thistle, sunflower, borage or plants such as maize, wheat, rye, oats, triticale, rice, barley, cotton, cassava, pepper, tagetes, *Solanaceae* plants such as potato, tobacco, aubergine and tomato, *Vicia* species, pea, alfalfa, shrub plants (coffee, cacao, tea), *Salix* species, trees (oil palm, coconut) and perennial grasses and fodder crops. Especially preferred plants according to the invention are oil crops such as soybean, peanut, oilseed rape, canola, sunflower, safflower, trees (oil palm, coconut).

With regard to, for example, a nucleic acid sequence, an expression cassette (=gene construct) or a vector comprising said nucleic acid sequence or an organism transformed with the nucleic acid sequences, expression cassette or vector according to the invention, "transgenic" refers to all those constructions which have been brought about by recombinant methods in which either a) the nucleic acid sequence of the invention, or
b) a genetic control sequence in operable linkage with the nucleic acid sequence according to the invention, for example a promotor, or
c) (a) and (b)

are not in their natural genetic environment or have been modified by recombinant methods, an example of a modification which is possible being a substitutions, additions, deletions, inversion or insertions of one or more nucleotide residues. "Natural genetic environment" refers to the natural chromosomal locus in the source organism or the presence in a genomic library. In the case of a genomic library, the natural genetic environment of the nucleic acid sequence is preferably retained at least in part. The environment flanks the nucleic acid sequence at least unilaterally and has a sequence length of at least 50 bp, preferably at least 500 bp, especially preferably at least 1000 bp, very especially preferably at least 5000 bp. A naturally occurring expression cassette—for example the naturally occurring combination of the natural promoter of the nucleic acid sequence according to the invention with the PSE gene in question— becomes a transgenic expression cassette when the latter is modified by nonnatural, synthetic ("artificial") methods such as, for example, mutagenic treatment. Such methods have been described for example in U.S. Pat. No. 5,565,350 or WO 00/15815.

The invention furthermore relates to transgenic organisms transformed with at least one nucleic acid sequence, expression cassette or vector according to the invention, and to cells, cell cultures, tissues, parts—such as, for example, in the case of plant organisms leaves, roots and the like—or propagation material derived from such organisms.

D. Isolated PSE

A further aspect of the invention relates to isolated PSEs and biologically active parts thereof. An "isolated" or "purified" protein or a biologically active part thereof, is essentially free of cellular material when it is produced by recombinant DNA techniques, or free of chemical precursors or other chemicals when it is synthesized chemically. The term "essentially free of cellular material" comprises PSE preparations in which the protein is separate from cellular components of the cells in which it is produced naturally or recombinantly. In one embodiment, the term "essentially free of cellular material" comprises PSE preparations with less than approximately 30% (based on the dry weight) of non-PSE (also referred to herein as "contaminating protein"), more preferably less than approximately 20% of non-PSE, even more preferably less than approximately 10% of non-PSE and most preferably less than approximately 5% of non-PSE. When the PSE or a biologically active part thereof has been produced by recombinant technology, it is also essentially free of culture medium, i.e. the culture medium amounts to less than approximately 20%, more preferably less than approximately 10% and most preferably less than approximately 5% of the volume of the protein preparation. The term "essentially free of chemical precursors or other chemicals" comprises PSE preparations in which the protein is separate from chemical precursors or other chemicals which are involved in the synthesis of the protein. In one embodiment, the term "essentially free of chemical precursors or other chemicals" comprises PSE preparations with less than approximately 30% (based on the dry weight) of chemical precursors or non-PSE chemicals, more preferably less than approximately 20% of chemical precursors or non-PSE chemicals, even more preferably less than approximately 10% of chemical precursors or non-PSE chemicals and most preferably less than approximately 5% of chemical precursors or non-PSE chemicals. In preferred embodiments, isolated proteins or biologically active parts thereof exhibit no contaminating proteins from the same organism from which the PSE originates. These proteins are usually produced by recombinant expression, for example of a *Phytophthora infestans* PSE in other fungi, plants or microorganisms for example bacteria such as *C. glutamicum*, fungi such as *Mortierella*, yeast such as *Saccharomyces*, or ciliates, algae such as *Phycomitrella patens*, or oil crops.

An isolated PSE according to the invention or part thereof can also participate in the metabolism of compounds required for the synthesis of cell membrans in *Phytophthora infestans* or in the transport of molecules via these membranes, or be involved in the fatty acid metabolism, or has one or more of the activities stated in Table I. In preferred embodiments, the protein or the part thereof comprises an amino acid sequence which has sufficient homology with an amino acid sequence of SEQ ID NO:2 for the protein or the part thereof to retain the ability to participate in the metabolism of compounds required for the synthesis of cell membranes in *Phytophthora infestans* or in the transport of molecules via these membranes or in the fatty acid metabolism. The part of the protein is preferably a biologically active part as described herein. In a further preferred embodiment, a PSE according to the invention has one of the amino acid sequences shown in SEQ ID NO:2. In a further preferred embodiment, the PSE has an amino acid sequence which is encoded by a nucleotide sequence which hybridizes with a nucleotide sequence of SEQ ID NO:1, for example under stringent conditions. In yet another preferred embodiment, the PSE has an amino acid sequence encoded by a nucleotide sequence which has at least approximately 50 to 60%, preferably at least approximately 60 to 70%, more preferably at least approximately 70 to 80%, 80 to 90%, 90 to 95% and even more preferably at least approximately 96%, 97%, 98%, 99% or more homology with one of the amino acid sequences of SEQ ID NO:2. The PSE preferred in accordance with the invention preferably also has at least one of the PSE activities described herein. For example, a preferred PSE according to the invention comprises an amino acid sequence encoded by a nucleotide sequence which hybridizes with a nucleotide sequence of SEQ ID NO:1, for example under stringent conditions, and which can participate in the metabolism of compounds required for the synthesis of cell membranes in *Phytophthora infestans* or in the transport of molecules via these membranes or be involved in the fatty acid metabolism, or has one or more of the activities stated in Table I.

In other embodiments, the PSE is essentially homologous with an amino acid sequence of SEQ ID NO:2 and retains the functional activity of the protein of one of the sequences of SEQ ID NO:2, but its amino acid sequence differs, owing to natural variation or mutagenesis as described in detail in the above subsection I. In a further embodiment, the PSE is, accordingly, a protein comprising an amino acid sequence which has at least approximately 50 to 60%, preferably at least approximately 60 to 70% and more preferably at least approximately 70 to 80%, 80 to 90%, 90 to 95% and most preferably at least approximately 96%, 97%, 98%, 99% or more homology with a complete amino acid sequence of SEQ ID NO:2 and has at least one of the PSE activities described herein. In another embodiment, the invention relates to a complete *Phytophthora infestans* protein which is essentially homologous with a complete amino acid sequence of SEQ ID NO:2.

Biologically active parts of a PSE comprise peptides comprising amino acid sequences derived from the amino acid sequence of a PSE, for example an amino acid sequence shown in SEQ ID NO:2, or the amino acid sequence of a protein which is homologous with a PSE, which peptides have fewer amino acids than the full-length PSE or the full-length protein which is homologous with a PSE and have at least one activity of a PSE. Biologically active parts (peptides, for example peptides with a length of, for example, 5, 10, 15, 20, 30, 35, 36, 37, 38, 39, 40, 50, 100 or more amino acids) usually comprise a domain or a motif with at least one activity of a PSE. Moreover, other biologically active parts in which other regions of the protein are deleted can be generated by recombinant techniques and studied with regard to one or more of the activities described herein. The biologically active parts of a PSE preferably comprise one or more selected domains/motifs or parts thereof with biological activity.

PSEs are preferably produced by recombinant DNA techniques. For example, a nucleic acid molecule encoding the protein is cloned into an expression vector (as described above), the expression vector is introduced into a host cell (as described above), and the PSE is expressed in the host cell. The PSE can then be isolated from the cells by a suitable purification scheme using standard techniques of protein purification. As an alternative to the recombinant expression, a PSE, a PSE polypeptide or a PSE peptide can be synthesized chemically by standard techniques of peptide synthesis. Moreover, native PSE can be isolated from cells (for example endothelial cells), for example using an anti-PSE antibody which can be raised by standard techniques, using a PSE according to the invention or a fragment thereof.

The invention also provides chimeric PSE proteins or PSE fusion proteins. As used in the present context, a "chimeric PSE protein" or "PSE fusion protein" comprises a PSE polypeptide which is operably bound to a non-PSE polypeptide. A "PSE polypeptide" refers to a polypeptide with an amino acid sequence which corresponds to a PSE, while a "non-PSE polypeptide" refers to a polypeptide with an amino acid sequence which corresponds to a protein which is essentially not homologous with PSE, for example a protein which differs from PSE and which originates from the same or another organism. Within the fusion protein, the term "operably linked" is to be understood as meaning that the PSE polypeptide and the non-PSE polypeptide are fused to each other in such a way that both sequences fulfill the predicted function which has been ascribed to the sequence used. The non-PSE polypeptide can be fused to the N terminus or the C terminus of the PSE polypeptide. In one embodiment the fusion protein is, for example, a GST-PSE fusion protein in which the PSE sequences are fused to the C terminus of the GST sequences. These fusion proteins can facilitate the purification of the recombinant PSEs. In a further embodiment, the fusion protein is a PSE which has a heterologous signal sequence at its N terminus. In certain host cells (for example mammalian host cells), expression and/or secretion of a PSE can be increased by using a heterologous signal sequence.

A chimeric PSE protein or PSE fusion protein according to the invention is produced by standard recombinant DNA techniques. For example, DNA fragments which encode different polypeptide sequences are ligated to each other in correct reading frame using conventional techniques, for example by employing blunt ends or overhanging ends for ligation, restriction enzyme cleavage for providing suitable ends, filling up cohesive ends, as required, treatment with alkaline phosphatase to avoid undesired linkages, and enzymatic ligation. In a further embodiment, the fusion gene can be synthesized by conventional techniques including DNA synthesizers. As an alternative, PCR amplification of gene fragments can be carried out using anchor primers which generate complementary overhangs between successive gene fragments which can subsequently be mutually hybridized and reamplified to give rise to a chimeric gene sequence (see, for example, Current Protocols in Molecular Biology, Ed. Ausubel et al., John Wiley & Sons: 1992). Moreover, a large number of expression vectors which already encode a fusion unit (for example a GST polypeptide) are commercially available. PSE-encoding nucleic acid can be cloned into such an expression vector so that the fusion unit is linked in correct reading frame to the PSE protein.

PSE homologs can be generated by mutagenesis, for example by specific point mutation or truncating the PSE. The term "homolog" as used in the present context refers to a variant form of PSE which acts as agonist or antagonist of the PSE activity. A PSE agonist can essentially retain the same activity as PSE, or some of the biological activities. A PSE antagonist can inhibit one or more activities of the naturally occurring PSE form, for example by competitive binding to an upstream or downstream element of the metabolic cascade for cell membrane components which comprises the PSE, or by binding to a PSE which mediates the transport of compounds via cell membranes, thus inhibiting translocation.

In an alternative embodiment, PSE homologs can be identified by screening combinatory libraries of mutants, for example truncated mutants, of PSE with regard to PSE agonist or PSE antagonist activity. In one embodiment, a variegated library of PSE variants is generated at the nucleic acid level by combinatory mutagenesis and encoded by a variegated genetic library. A variegated library of PSE variants can be generated for example by enzymatic ligation of a mixture of synthetic oligonucleotides into gene sequences so that a degenerate set of potential PSE sequences can be expressed as individual polypeptides or, alternatively, as a set of larger fusion proteins (for example for phage display) which comprise this set of PSE sequences. There is a multiplicity of methods which can be used for generating libraries of potential PSE homologs from a degenerate oligonucleotide sequence. The chemical synthesis of a degenerate gene sequence can be carried out in a DNA synthesizer, and the synthetic gene can then be ligated into a suitable expression vector. The use of a degenerate set of genes allows all sequences which encode the desired set of potential PSE sequences to be provided in a mixture. Methods for the synthesis of degenerate oligonucleotides are known in the art (see, for example, Narang, S. A. (1983) Tetrahedron 39:3; Itakura et al. (1984) Annu. Rev. Biochem. 53:323; Itakura et al., (1984) Science 198: 1056; Ike et al. (1983) Nucleic Acids Res. 11:477).

In addition, libraries of PSE fragments can be used for generating a variegated population of PSE fragments for screening and for the subsequent selection of homologs of a PSE. In one embodiment, a library of fragments of the coding sequence can be generated by treating a double-stranded PCR fragment of a coding PSE sequence with a nuclease under conditions under which double-strand breaks only occur approximately once per molecule, denaturing the double-stranded DNA, renaturing the DNA with the formation of double-stranded DNA which can comprise sense/antisense pairs of various products with double-strand breaks, removal of single-stranded sections from newly formed duplices by treatment with S1 nuclease, and ligating the resulting fragment library into an expression vector. This method allows an expression library to be derived which encodes N-terminal, C-terminal and internal fragments of variously sized PSEs.

A number of techniques for screening gene products in combinatory libraries which have been generated by point mutations or truncation and for screening cDNA libraries for gene products with a selected property are known in the art. These techniques can be adapted to rapid screening of the genetic libraries which have been generated by combinatory mutagenesis of PSE homologs. The most frequently used techniques for screening large genetic libraries which can be subjected to high-throughput analysis usually comprise cloning the genetic library into replicable expression vectors, transforming suitable cells with the resulting vector library, and expressing the combinatory genes under conditions under which detecting the desired activity facilitates the isolation of the vector encoding the gene whose product has been detected. Recursive ensemble mutagenese (REM), a novel technique which increases the frequency of functional mutants in the libraries, can be used in combination with the screening assays for identifying PSE homologs (Arkin and Yourvan (1992) Proc. Natl. Acad. Sci. USA 89:7811–7815; Delgrave et al. (1993) Protein Engineering 6(3):327–331).

In a further embodiment, cell-based assays can be made use of for analyzing a variegated PSE library using processes known in the art.

E. Uses and Processes/Methods According to the Invention

The nucleic acid molecules, proteins, protein homologs, fusion proteins, primers, vectors and host cells described herein can be used in one or more of the methods which follow: identification of *Phytophthora infestans* and related organisms, genome mapping of organisms which are related to *Phytophthora infestans*, identification and localization of *Phytophthora infestans* sequences of interest, evolutionary studies, determination of PSE protein regions required for the function, modulation of a PSE activity; modulation of the metabolism of one or more cell membrane components; modulation of the transmembrane transport of one or more compounds, and modulation of the cellular production of a desired compound such as a fine chemical. The PSE nucleic acid molecules according to the invention have a multiplicity of uses. Firstly, they can be used for identifying an organism as *Phytophthora infestans* or a close relative thereof. They can also be used for identifying the presence of *Phytophthora infestans* or a relative thereof in a mixed population of microorganisms. The invention provides the nucleic acid sequences of a series of *Phytophthora infestans* genes; the presence or absence of this organism can be determined by screening the extracted genomic DNA of a culture of a uniform or mixed population of microorganisms under stringent conditions with a probe covering a region of a *Phytophthora infestans* gene which is unique for this organism, or of parts of this gene. While *Phytophthora infestans* itself is not used for the commercial production of polyunsaturated acids, Oomycetes are suitable in principle for the production of PUFAs. This is why PSE-related DNA sequences are particularly suitable for use in the PUFA production in other organisms.

Furthermore, the nucleic acid and protein molecules according to the invention can act as markers for specific regions of the genome. They are not only suitable for mapping the genome, but also for functional studies of *Phytophthora infestans* proteins. To identify the genome region to which a certain DNA-binding protein of *Phytophthora infestans* binds, the *Phytophthora infestans* genome might be fragmented, for example, and the fragments incubated with the DNA-binding protein. Those which bind the protein can additionally be screened with the nucleic acid molecules according to the invention, preferably with readily detectable markers; the binding of such a nucleic acid molecule to the genome fragment makes possible the localization of the fragment on the genome map of *Phytophthora infestans* and, if this is carried out repeatedly with different enzymes, facilitates a rapid determination of the nucleic acid sequence to which the protein binds. Moreover, the nucleic acid molecules according to the invention can have sufficient homology with the sequences of related species for these nucleic acid molecules to be able to act as markers for the construction of a genomic map in related fungi.

The PSE nucleic acid molecules according to the invention are also suitable for evolutionary studies and studies of the protein structure. The metabolic and transport processes in which the molecules according to the invention are involved are utilized by a large number of prokaryotic and eukaryotic cells; the evolutionary degree of relatedness of the organisms can be determined by comparing the sequences of the nucleic acid molecules according to the invention with those which encode similar enzymes from other organisms. Accordingly, such a comparison allows the determination of which sequence regions are conserved and which are not conserved, which may be helpful when determining regions of the protein which are essential for enzyme function. This type of determination is valuable for protein engineering studies and may provide a clue of how much mutagenesis the protein can tolerate without losing its function.

Manipulation of the PSE nucleic acid molecules according to the invention can lead to the production of PSEs with functional differences to the wild-type PSEs. The efficacy or activity of these proteins can be improved; they may be present in the cell in larger numbers than usual; or their efficacy or activity can be reduced. An improved efficacy or activity means, for example, that the enzyme has a higher selectivity and/or activity, preferably an activity which is at least 10% higher, very especially an activity which is at least 20% higher, very especially preferably an activity which is at least 30% higher, than the original enzyme.

There exists a series of mechanisms by which modification of a PSE according to the invention can directly affect yield, production and/or production efficacy of a fine chemical comprising such a modified protein. Obtaining fine chemical compounds from cultures of ciliates, algae, plants or fungi on a large scale is significantly improved when the cell secretes the desired compounds, since these compounds can readily be isolated from the culture medium (in contrast to extraction from the biomass of the cultured cells). Otherwise, purification can be improved when the cell stores compounds in vivo in a specialized compartment with a sort of concentration mechanism. In plants which express PSEs, an increased transport may lead to better distribution within the plant tissue and the plant organs. Increasing the number or the activity of the transporter molecules which export fine chemicals from the cell may allow the quantity of the fine chemical produced, which is present in the extracellular medium, to be increased, thus facilitating harvesting and purification or, in the case of plants, more efficient distribution. In contrast, increased amounts of cofactors, precursor molecules and intermediates for the suitable biosynthetic pathways are required for an efficient overproduction of one or more fine chemicals. Increasing the number and/or the activity of transporter proteins involved in the import of nutrients such as carbon sources (i.e. sugars), nitrogen sources (i.e. amino acids, ammonium salts), phosphate and sulfur can improve the production of a fine chemical owing to the elimination of all limitations of the nutrients available in the biosynthetic process. Fatty acids such as PUFAs and lipids comprising PUFAs are desirable fine chemicals themselves; optimizing the activity or increasing the number of one or more PSEs according to the invention involved in the biosynthesis of these compounds, or disrupting the activity of one or more PSEs involved in the breakdown of these compounds, can thus increase the yield, production and/or production efficacy of fatty acid and lipid molecules in ciliates, algae, plants, fungi, yeasts or other microorganisms.

The manipulation of one or more PSE genes according to the invention can likewise lead to PSEs with modified activities which indirectly affect the production of one or more desired fine chemicals from algae, plants, ciliates or fungi. The normal biochemical metabolic processes lead, for example, to the production of a multiplicity of waste products (for example hydrogen peroxide and other reactive oxygen species) which can actively disrupt these metabolic processes (for example, peroxynitrite is known to nitrate tyrosine side chains, thus inactivating some enzymes with tyrosine in the active center (Groves, J. T. (1999) Curr. Opin. Chem. Biol. 3(2);226–235). While these waste products are normally excreted, the cells used for fermentative production on a large scale are optimized for the overproduction of one or more fine chemicals and can therefore produce more waste products than is customary for a wild-type cell. Optimizing the activity of one or more PSEs according to the invention which are involved in the export of waste molecules allows the improvement of the viability of the cell and the maintenance of an efficient metabolic activity. Also, the presence of high intracellular amounts of the desired fine chemical can in fact be toxic to the cell, so that the viability of the cell can be improved by increasing the ability of the cell to secrete these compounds.

Furthermore, the PSEs according to the invention can be manipulated in such a way that the relative amounts of various lipid and fatty acid molecules are modified. This can have a decisive effect on the lipid composition of the cell membrane. Since each lipid type has different physical properties, the modification of the lipid composition of a membrane can significantly modify membrane fluidity. Changes in membrane fluidity can affect the transport of molecules via the membrane which, as explained above, can modify the export of waste products or of the fine chemical produced or the import of nutrients which are required. These changes in membrane fluidity can also have a decisive effect on cell integrity; cells with comparatively weaker membranes are more susceptible to abiotic and biotic stress conditions which can damage or kill the cell. Manipulation of PSEs which are involved in the production of fatty acids and lipids for membrane synthesis so that the resulting membrane has a membrane composition which is more susceptible to the environmental conditions prevailing in the cultures used for the production of fine chemicals should allow more cells to survive and multiply. Larger numbers of producing cells should manifest themselves in greater yields, higher production or higher production efficacy of the fine chemical from the culture.

The abovementioned mutagenesis strategies for PSEs intended to lead to elevated yields of a fine chemical are not to be construed as limiting; variations of these strategies are readily obvious to the skilled worker. Using these mechanisms, and with the aid of the mechanisms disclosed herein, the nucleic acid and protein molecules according to the invention can be used for generating recombinant or transgenic algae, ciliates, plants, nonhuman animals, fungi or other microorganisms such as *C. glutamicum* which express mutated PSE nucleic acid and protein molecules so that the yield, production and/or production efficacy of a desired compound is improved. This desired compound can be any natural product of algae, ciliates, plants, animals, fungi or *C. glutamicum* which comprises the end products of biosynthetic pathways and intermediates of naturally occurring metabolic pathways, and also molecules which do not naturally occur in the metabolism of these cells, but which are produced by the cells according to the invention.

A further embodiment according to the invention is a process for the production of PUFAs, which comprises culturing an organism which comprises a nucleic acid according to the invention, a gene construct according to the invention or a vector according to the invention which encode a polypeptide which elongates $C_{16}$- and/or $C_{18}$-fatty acids with at least two double bonds in the fatty acid molecule by at least two carbon atoms under conditions under which PUFAs are produced in the organism. PUFAs prepared by this process can be isolated by harvesting the organisms either from the culture in which they grow or from the field, and disrupting and/or extracting the harvested material with an organic solvent. The oil, which contains lipids, phospholipids, sphingolipids, glycolipids, triacylglycerols and/or free fatty acids with a higher PUFA content, can be isolated from this solvent. The free fatty acids with a higher content of PUFAs can be isolated by basic or acid hydrolysis of the lipids, phospholipids, sphingolipids, glycolipids and triacylglycerols. A higher content of PUFAs means at least 5%, preferably 10%, especially preferably 20%, very especially preferably 40% more PUFAs than the original organism, for example an Oomycete such as *Phytophthora* or a plant such as an oil crop plant, which does not have additional nucleic acid encoding the elongase according to the invention. Moreover, the abovementioned oils, lipids, phospholipids, sphingolipids, glycolipids, triacylglycerols and/or free fatty acids with a higher PUFA content have a different composition than the composition of starting organisms. This applies in particular to plants which do not naturally comprise longer-chain polyunsaturated $C_{20}$- or $C_{22}$-fatty acids such as DHA, EPA or ARA.

The PUFAs produced by this process are preferably $C_{20}$- or $C_{22}$-fatty acid molecules with at least two double bonds in the fatty acid molecule, preferably three or four double bonds, especially preferably three double bonds. These $C_{20}$- or $C_{22}$-fatty acid molecules can be isolated from the organism in the form of an oil, lipid or a free fatty acid. Examples of suitable organisms are those mentioned above. Preferred organisms are transgenic plants.

An embodiment according to the invention are oils, lipids or fatty acids or fractions thereof which have been prepared by the above-described process, especially preferably oil, lipid or a fatty acid composition comprising PUFAs and originating from transgenic plants.

A further embodiment according to the invention is the use of the oil, lipid or the fatty acid composition in feeding stuffs, foodstuffs, cosmetics or pharmaceuticals.

This invention is illustrated in greater detail by the examples which follow, which are not to be construed as limiting. The content of all references, patent applications, patents and published patent applications cited in this patent application is incorporated herein by reference.

EXAMPLES

Example 1

General Methods a) General Cloning Methods:

Cloning methods, such as, for example, restriction cleavages, agarose gel electrophoresis, purification of DNA fragments, transfer of nucleic acids to nitrocellulose and nylon membranes, linkage of DNA fragments, transformation of *Escherichia coli* and yeast cells, the culture of bacteria and the sequence analysis of recombinant DNA were carried out as described in Sambrook et al. ((1989), Cold Spring Harbor Laboratory Press: ISBN 0-87969-309-6) or Kaiser, Michaelis and Mitchell ((1994), "Methods in Yeast Genetics", Cold Spring Harbor Laboratory Press: ISBN 0-87969-451-3).

b) Chemicals

Unless otherwise specified in the text, the chemicals used were obtained in analytical grade quality from Fluka (Neu-Ulm), Merck (Darmstadt), Roth (Karlsruhe), Serva (Heidelberg) and Sigma (Deisenhofen). Solutions were prepared using pure pyrogen-free water, referred to in the following text as $H_2O$, from a Milli-Q water system water purification unit (Millipore, Eschborn). Restriction endonucleases, DNA-modifying enzymes and molecular biology kits were obtained from AGS (Heidelberg), Amersham (Brunswick), Biometra (Göttingen), Boehringer (Mannheim), Genomed (Bad Oeynhausen), New England Biolabs (Schwalbach/Taunus), Novagen (Madison, Wis., USA), Perkin-Elmer (Weiterstadt), Pharmacia (Freiburg), Qiagen (Hilden) and Stratagene (Amsterdam, Netherlands). Unless otherwise specified, they were used following the manufacturer's instructions.

Example 2

Construction of the cDNA Library

To construct the cDNA library, the first-strand synthesis was carried out using murine leukemia virus reverse transcriptase (Roche, Mannheim, Germany) and oligo-d(T) primers, while the second-strand synthesis was carried out by incubation with DNA polymerase I, Klenow enzyme and cleavage with RNAse H at 12° C. (2 hours), 16° C. (1 hour) and 22° C. (1 hour). The reaction was quenched by incubation at 65° C. (10 minutes) and subsequently transferred to ice. Double-stranded DNA molecules were made blunt-ended with T4 DNA polymerase (Roche, Mannheim) at 37° C. (30 minutes). The nucleotides were removed by extraction with phenol/chloroform and Sephadex G50 spin columns. EcoRI adapters (Pharmacia, Freiburg, Germany) were ligated to the cDNA ends by means of T4 DNA ligase (Roche, 12° C., overnight) and phosphorylated by incubation with polynucleotide kinase (Roche, 37° C., 30 minutes). This mixture was subjected to separation on a low-melting agarose gel. DNA molecules of over 300 base pairs were eluted from the gel, extracted with phenol, concentrated on Elutip D columns (Schleicher and Schüll, Dassel, Germany), ligated to vector arms and packaged into lambda-ZAPII phages or lambda-ZAP-express phages using the Gigapack Gold kit (Stratagene, Amsterdam, the Netherlands), using the manufacturer's material and following their instructions.

Example 3

DNA Sequencing and Computer Analysis cDNA libraries as described in Example 4 were used for DNA sequencing by standard methods, in particular the chain termination method using the ABI PRISM Big Dye Terminator Cycle Sequencing Ready Reaction kit (Perkin-Elmer, Weiterstadt, Germany). Following the plasmid preparation from cDNA libraries, clones were random-sequenced via an in-vivo mass excision and retransformation of DH10B on agar plates (details on materials and protocol: Stratagene, Amsterdam, the Netherlands). Plasmid DNA was prepared from *E. coli* cultures grown overnight in Luria broth supplemented with ampicillin (see Sambrook et al. (1989) (Cold Spring Harbor Laboratory Press: ISBN 0-87969-309-6)) using a Qiagen DNA preparation robot (Qiagen, Hilden) following the manfucturer's protocols. Sequencing primers with the following nucleotide sequences were used:

```
5'-CAGGAAACAGCTATGACC-3'

5'-CTAAAGGGAACAAAAGCTG-3'

5'-TGTAAAACGACGGCCAGT-3'
```

The sequences were processed and commented using the EST-MAX standard software package which is commercially available from Bio-Max (Munich, Germany). One clone with weak homologies with known elongases was characterized in greater detail.

Example 4

Identification of the *P. infestans* PSE1 Gene, and Analysis of the cDNA Clone PiPSE1

An EST sequence (database entry: PI001002014r) was considered as target gene, among other candidate genes, owing to weak homology with known elongases.

The BESTFIT program, i.e. the BLOSUM amino acid substitution matrices, was used for the sequence alignment, reference being made to Henikoff, S., and Henikoff, J. G. (1992), Amino acid substitution matrices from protein blocks, Proc. Natl. Acad. Sci. USA 89:10915–10919.

The sequence of the clone with the database No. PI001002014r was used for the alignment with the yeast elo1 peptide sequence. Since the novel *P. infestans* clone was not complete, the corresponding full-length clone (PiPSEI) was isolated, starting from the *P. infestans* cDNA library. To this end, a digoxigenin-labeled probe was generated by PCR by means of the PCR DIG synthesis kit (Roche), with PI001002014 being used as the template. The following primers were used for the PCR:

PI-DIGf: cacaccatcatgtacacttactac

PI-DIGr: caacttcttcttcgattcctccac

The isolated labeled probe was used for screening the *P. infestans* cDNA library (in accordance with the manufacturer, Stratagene). A 1046 bp fragment was isolated and named PiPSE1. The open reading frame is 837 bp in length and encodes a protein of 278 amino acids with calculated molar mass of 32.1 kDa. Sequence alignments revealed the following sequence identities and sequence similarities, respectively: 26%/43% with the *Physcomitrella patens* PSE1p, 23%/37% with the human HELOp, 21%/41% with the *Mortierella alpina* GLELOp and 17%/36% with the *C. elegans* elongase.

Example 5

Identification of Genes by Means of Hybridization

Gene sequences can be used for identifying homologous or heterologous genes from cDNA libraries or genomic libraries.

Homologous genes (i.e. full-length cDNA clones which are homologous, or homologs) can be isolated via nucleic acid hybridization using, for example, cDNA libraries. Depending on the frequency of the gene of interest, 100 000 up to 1 000 000 recombinant bacteriophages were plated and transferred to a nylon membrane. After denaturation with alkali, the DNA was immobilized on the membrane, for example by UV crosslinking. Hybridization was performed under highly stringent conditions. The hybridization and the wash steps were carried out in aqueous solution at an ionic strength of 1 M NaCl and a temperature of 68° C. Hybridization probes were generated for example by labeling with radioactive (32p–) nick transcription (High Prime, Roche, Mannheim, Germany). The signals were detected by autoradiography.

Partially homologous or heterologous genes which are related but not identical can be identified analogously to the process described above using low-stringency hybridization and wash conditions. For the aqueous hybridization, the ionic strength was usually kept at 1 M NaCl, and the temperature was lowered gradually from 68 to 42° C.

The isolation of gene sequences which only exhibit homologies with an individual domain of, for example, 10 to 20 amino acids can be carried out using synthetic, radiolabeled oligonucleotide probes. Radiolabeled oligonucleotides were generated by phosphorylating the 5' end of two complementary oligonucleotides with T4 polynucleotide kinase. The complementary oligonucleotides were hybridized and ligated with each other to give rise to concatemers. The double-stranded concatemers were radiolabeled for example by nick transcription. Hybridization was usually carried out under low stringency conditions using high oligonucleotide concentrations.

Oligonucleotide Hybridization Solution:
6×SSC
0.01 M sodium phosphate
1 mM EDTA (pH 8)
0.5% SDS
100 αg/ml denatured salmon sperm DNA
0.1% dry low-fat milk During the hybridization, the temperature was lowered in steps to 5 to 10° C. below the calculated oligonucleotide temperature or to room temperature (unless otherwise specified, RT=~23° C. in all experiments), followed by wash steps and autoradiography. Washing was carried out at extremely low stringency, for example 3 wash steps using 4×SSC. Further details are described by Sambrook, J., et al. (1989), "Molecular Cloning: A Laboratory Manual", Cold Spring Harbor Laboratory Press, or Ausubel, F. M., et al. (1994) "Current Protocols in Molecular Biology", John Wiley & Sons.

Preparation of specific antibodies, for example under

Example 6

Northern Hybridization

For the RNA hybridization, 20 μg of total RNA or 1 μg of poly(A)$^+$-RNA were separated by gel electrophoresis in 1.25% strength agarose gels using formaldehyde as described by Amasino (1986, Anal. Biochem. 152, 304), transferred to positively charged nylon membranes (Hybond N+, Amersham, Brunswick) by capillary attraction using 10×SSC, immobilized by UV light and prehybridized for 3 hours at 68° C. using hybridization buffer (10% dextran sulfate w/v, 1 M NaCl, 1% SDS, 100 mg herring sperm DNA). The DNA probe had been labeled with the Highprime DNA labeling kit (Roche, Mannheim, Germany) during the prehybridization stage using alpha-$^{32}$P-dCTP (Amersham, Brunswick, Germany). The hybridization was carried out after adding the labeled DNA probe in the same buffer at 68° C. overnight. The wash steps were carried out twice for 15 minutes using 2×SSC and twice for 30 minutes using 1×SSC, 1% SDS, at 68° C. The sealed filters were exposed at −70° C. for a period of 1 to 14 days.

Example 7

Plasmids for Plant Transformation

Binary vectors such as pBinAR can be used for plant transformation (Höfgen and Willmitzer, Plant Science 66 (1990) 221–230). The binary vectors can be constructed by ligating the cDNA in sense or antisense orientation into T-DNA. 5' of the cDNA, a plant promoter activates cdNA transcription. A polyadenylation sequence is located 3' of the cDNA.

Tissue-specific expression can be achieved using a tissue-specific promoter. For example, seed-specific expression can be achieved by cloning in the napin or the LeB4 or the USP promotor 5' of the cDNA. Any other seed-specific promoter element can also be used. The CaMV 35S promotor may be used for constitutive expression in all of the plant.

The protein expressed can be targeted into a cellular compartment using a signal peptide, for example for plastids, mitochondria or the endoplasmic reticulum (Kermode, Crit. Rev. Plant Sci. 15, 4 (1996) 285–423). The signal peptide is cloned 5' in correct reading frame with the cDNA in order to achieve subcellular localization of the fusion protein.

Example 8

Transformation of Agrobacterium

Agrobacterium-mediated plant transformation can be carried out for example using the Agrobacterium tumefaciens strain GV3101 (pMP90) (Koncz and Schell, Mol. Gen. Genet. 204 (1986) 383–396) or LBA4404 (Clontech). The transformation can be carried out by standard transformation techniques (Deblaere et al., Nucl. Acids. Tes. 13 (1984), 4777–4788).

Example 9

Plant Transformation

Agrobacterium-mediated plant transformation can be carried out using standard transformation and regeneration techniques (Gelvin, Stanton B., Schilperoort, Robert A., Plant Molecular Biology Manual, 2nd Edition, Dordrecht: Kluwer Academic Publ., 1995, in Sect., Ringbuch Zentrale Signatur: BT11-P ISBN 0-7923-2731-4; Glick, Bernard R., Thompson, John E., Methods in Plant Molecular Biology and Biotechnology, Boca Raton: CRC Press, 1993, 360 pp., ISBN 0-8493-5164-2).

For example, oilseed rape can be transformed by means of cotyledon or hypocotyledon transformation (Moloney et al., Plant Cell Report 8 (1989) 238–242; De Block et al., Plant Physiol. 91 (1989) 694–701). The use of antibiotics for the selection of agrobacteria and plants depends on the binary vector and agrobacterial strain used for the transformation. The selection of oilseed rape is normally carried out using kanamycin as selectable plant marker.

Agrobacterium-mediated gene transfer in flax can be carried out for example using a technique described by Mlynarova et al. (1994) Plant Cell Report 13:282–285.

The transformation of soybean can be carried out for example using a technique described in EP-A-0 424 047 (Pioneer Hi-Bred International) or in EP-A-0 397 687, U.S. Pat. No. 5,376,543, 5,169,770 (University Toledo).

Plant transformation using particle bombardment, polyethylene-glycol-mediated DNA uptake or via the silicon carbonate fiber technique is described, for example, by Freeling and Walbot "The maize handbook" (1993) ISBN 3-540-97826-7, Springer Verlag N.Y.).

Example 10

In Vivo Mutagenesis

The in vivo mutagenesis of microorganisms can be performed by passing the plasmid DNA (or any other vector DNA) via E. coli or other microorganisms (e.g. Bacillus spp. or yeasts such as Saccharomyces cerevisiae), in which the ability of retaining the integrity of their genetic information is disrupted. Conventional mutator strains have mutations in the genes for the DNA repair system (for example mutHLS, mutD, mutT and the like; as reference, see Rupp, W. D. (1996) DNA repair mechanisms, in: Escherichia coli and Salmonella, pp. 2277–2294, ASM: Washington). These strains are known to the skilled worker. The use of these strains is illustrated for example in Greener, A., and Callahan, M. (1994) Strategies 7:32–34. Mutated DNA molecules are preferably transferred to plants after the microorganisms have been selected and tested. Transgenic plants are generated in accordance with various examples in the examples section of the present document.

Example 11

Studying the Expression of a Recombinant Gene Product in a Transformed Organism The activity of a recombinant gene product in the transformed host organism was measured at the transcriptional and/or the translational level.

A suitable method for determining the amount of transcription of the gene (which indicates the amount of RNA available for translation of the gene product) is to carry out a northern blot (for reference, see Ausubel et al. (1988) Current Protocols in Molecular Biology, Wiley: New York, or the abovementioned examples section) in which a primer which is designed such that it binds to the gene of interest is labeled with a detectable label (usually radioactivity or chemiluminescence) so that, when the total RNA of a culture of the organism is extracted, separated on a gel, transferred to a stable matrix and incubated with this probe, binding and the extent of binding of the probe indicates the presence as well as the quantity of mRNA for this gene. This information indicates the degree of transcription of the transformed gene. Total cell RNA can be prepared from cells, tissues or organs by a plurality of methods, all of which are known in the art, such as, for example, the method of Bormann, E. R., et al. (1992) Mol. Microbiol. 6:317–326.

Standard techniques, such as a Western blot (see, for example, Ausubel et al. (1988) Current Protocols in Molecular Biology, Wiley: New York) can be employed for studying the presence or the relative quantity of protein translated by this mRNA. In this method, the total cell proteins are extracted, separated by means of gel electrophoresis, transferred to a matrix such as nitrocellulose and incubated with a probe such as an antibody which specifically binds to the desired protein. This probe is usually provided with a chemiluminescent or colorimetric label which can be detected readily. The presence and the quantity of the label observed indicates the presence and the quantity of the desired mutated protein which is present in the cell.

Example 12

Analysis of the Effect of the Recombinant Proteins on the Production of the Desired Product The effect of the genetic modification in plants, fungi, algae, ciliates or on the production of a desired compound (such as a fatty acid) can be determined by growing the modified microorganisms or the modified plant under suitable conditions (such as those described above) and analyzing the medium and/or the cell components for the increased production of the desired product (i.e. of lipids or a fatty acid). These analytical techniques are known to the skilled worker and include spectroscopy, thin-layer chromatography, various staining methods, enzymatic and microbiological methods, and analytical chromatography such as high-performance liquid chromatography (see, for example, Ullman, Encyclopedia of Industrial Chemistry, Vol. A2, pp. 89–90 and pp. 443–613, VCH Weinheim (1985); Fallon, A., et al., (1987) "Applications of HPLC in Biochemistry" in: Laboratory Techniques in Biochemistry and Molecular Biology, Vol. 17; Rehm et al. (1993) Biotechnology, Vol. 3, Chapter III "Product recovery and purification", pp. 469–714, VCH Weinheim; Belter, P. A., et al. (1988) Bioseparations: downstream processing for Biotechnology, John Wiley and Sons; Kennedy, J. F., and Cabral, J. M. S. (1992) Recovery processes for biological Materials, John Wiley and Sons; Shaeiwitz, J. A., and Henry, J. D. (1988) Biochemical Separations, in: Ullmann's Encyclopedia of Industrial Chemistry, Vol. B3; Chapter 11, pp. 1–27, VCH Weinheim; and Dechow, F. J. (1989) Separation and purification techniques in biotechnology, Noyes Publications).

In addition to the abovementioned methods, plant lipids are extracted from plant material as described by Cahoon et al. (1999) Proc. Natl. Acad. Sci. USA 96 (22):12935–12940, and Browse et al. (1986) Analytic Biochemistry 152:141–145. Qualitative and quantitative lipid or fatty acid analysis is described in Christie, William W., Advances in Lipid Methodology, Ayr/Scotland: Oily Press (Oily Press Lipid Library; 2); Christie, William W., Gas Chromatography and Lipids. A Practical Guide—Ayr, Scotland: Oily Press, 1989, Repr. 1992, IX, 307 pp. (Oily Press Lipid Library; 1); "Progress in Lipid Research, Oxford: Pergamon Press, 1 (1952)–16 (1977) under the title: Progress in the Chemistry of Fats and Other Lipids CODEN.

In addition to measuring the end product of the fermentation, it is also possible to analyze other components of the metabolic pathways which are used for producing the desired compound, such as intermediates and byproducts, in order to determine the overall production efficiency of the compound. The analytical methods include measurements of the nutrient quantities in the medium (for example sugars, carbohydrates, nitrogen sources, phosphate and other ions), biomass composition and growth measurements, analysis of the production of customary metabolites of biosynthetic pathways, and measurements of gases which are generated during fermentation. Standard methods for these measurements are described in Applied Microbial Physiology; A Practical Approach, P. M. Rhodes and P. F. Stanbury, Ed., IRL Press, pp. 103–129; 131–163 and 165–192 (ISBN: 0199635773) and references stated therein.

One example is the analysis of fatty acids (abbreviations: FAME, fatty acid methyl ester; GC-MS, gas-liquid chromatography/mass spectrometry; TAG, triacylglycerol; TLC, thin-layer chromatography).

The unambiguous detection of the presence of fatty acid products can be obtained by analyzing recombinant organisms by analytical standard methods: GC, GC-MS or TLC, as they are described on several occasions by Christie and the references therein (1997, in: Advances on Lipid Methodology, Fourth edition: Christie, Oily Press, Dundee, 119–169; 1998, gas chromatography/mass spectrometry methods, Lipide 33:343–353).

The material to be analyzed can be disrupted by sonication, grinding in a glass mill, liquid nitrogen and grinding or via other applicable methods. After disruption, the material must be centrifuged. The sediment is resuspended in distilled water, heated for 10 minutes at 100° C., ice-cooled and recentrifuged followed by extraction in 0.5 M sulfuric acid in methanol with 2% dimethoxypropane for 1 hour at 90° C., which leads to hydrolyzed oil and lipid compounds which give transmethylated lipids. These fatty acid methyl esters are extracted in petroleum ether and finally subjected to GC analysis using a capillary column (Chrompack, WCOT Fused Silica, CP-Wax-52 CB, 25 m, 0.32 mm) at a temperature gradient of between 170° C. and 240° C. for 20 minutes and 5 minutes at 240° C. The identity of the resulting fatty acid methyl esters must be defined using standards which are commercially available (i.e. Sigma).

In the case of fatty acids for which no standards are available, the identity must be demonstrated via derivatization followed by GC-MS analysis. For example, the localization of fatty acids with triple bond must be demonstrated via GC-MS following derivatization with 4,4-dimethoxyoxazolin derivatives (Christie, 1998, see above).

Example 13

Expression Constructs in Heterologous Microbial Systems

Strains, Growth Conditions and Plasmids

The *Escherichia coli* strain XL1 Blue MRF' kan (Stratagene) was used for subcloning the novel *Phytophthora infestans* elongase PiPSE1. For functionally expressing this gene, we used the *Saccharomyces cerevisiae* strain INVSc 1 (Invitrogen Co.). *E. coli* was cultured at 37° C. in Luria-Bertini broth (LB, Duchefa, Haarlem, the Netherlands). If necessary, ampicillin (100 mg/liter) was added, and 1.5% of agar (w/v) was added for solid LB media. *S. cerevisiae* was cultured at 30° C. either in YPG medium or in complete minimal medium without uracil (CMdum; see: Ausubel, F. M., Brent, R., Kingston, R. E., Moore, D. D., Seidman, J. G., Smith, J. A., Struhl, K., Albright, L. B., Coen, D. M., and Varki, A. (1995) Current Protocols in Molecular Biology, John Wiley & Sons, New York) together with 2% (w/v) of either raffinose or glucose. For solid media, 2% (w/v) of Bacto™ agar (Difco) were added. The plasmids used for cloning and expression were pUC18 (Pharmacia) and pYES2 (Invitrogen Co.).

Cloning and Expression of a PUFA-Specific Elongase From *Phytophthora infestans*

For the expression in yeast, the *Phytophthora infestans* cDNA clone piPSE1, which encodes the PUFA-specific elongase (PSE1) gene, was first modified in such a way that a KpnI restriction site and the yeast consensus sequence for highly effective translation (Kozak, M. (1986) Point mutations define a sequence flanking the AUG initiator codon that modulates translation by eukaryotic ribosomes, Cell 44, 283–292) was obtained next to the start codon and a XbaI restriction site was obtained which flanked the stop codon. To amplify the open reading frame, a primer pair which was complementary to its 5' and 3' ends was synthesized.

ppexlf: cggggtaccacataatgtcgactgagctactgcag ppexlr: cactagtctagattccaacttcttcttcgattcc The PCR reaction was carried out with plasmid DNA as matrix in a thermocycler (Biometra) with Pfu DNA (Stratagene) polymerase and the following temperature program: 3 minutes at 96° C. followed by 30 cycles with 30 seconds at 96° C., 30 seconds at 55° C. and 2 minutes at 72° C., 1 cycle with 10 minutes at 72° C. and stop at 4° C.

The correct size of 883 bp of the amplified DNA fragment was confirmed by agarose TBE gel electrophoresis. The amplified DNA was extracted from the gel using the QIAquick gel extraction kit (QIAGEN) and ligated into the SmaI restriction site of the dephosphorylated vector pUC18 using the Sure Clone Ligation Kit (Pharmacia) giving rise to pUCPSE1. Following the transformation of *E. coli* XL1 Blue MRF' kan, a DNA minipreparation (Riggs, M. G., & McLachlan, A. (1986) A simplified screening procedure for large numbers of plasmid mini-preparation. BioTechniques 4, 310–313) of transformants was carried out on 24 ampicillin-resistant, and positive clones were identified by means of BamHI restriction analysis. The sequence of the cloned PCR product was confirmed by resequencing using the ABI PRISM Big Dye Terminator Cycle Sequencing Ready Reaction Kit (Perkin-Elmer, Weiterstadt).

The plasmid DNA of pUC-PSE1 was additionally cleaved with KpnI/XbaI, and the resulting ~900 bp fragment was ligated into the KpnI/XbaI restriction site of the dephosphorylated yeast E. coli shuttle vector pYES2, giving rise to pY2PSE1. Following transformation of E. coli and DNA minipreparation from the transformants, the orientation of the DNA fragment in the vector was checked by cleavage with HindIII. One clone was grown with the Nucleobond® AX 500 plasmid DNA extraction kit (Macherey-Nagel, Düringen) for the DNA maxipreparation.

Saccharomyces INVSc1 was transformed with pY2PSE1 and pYES2 by means of a modified PEG/lithium acetate protocol (Ausubel et al., 1995). Following selection on CMdum agar plates supplemented with 2% glucose, in each case four pY2PSE11 transformants (pY2PSE1a-d) and one pYES2 transformant were selected for further culture and functional expression.

Functional Expression of an Elongase Activity in Yeast

Preculture:

20 ml of CMdum liquid medium with 2% (w/v) raffinose were inoculated with the transgenic yeast clones (pY2PSE1a-d, pYES2) and cultured for 3 days at 30° C., 200 rpm, until an optical density at 600 nm ($OD_{600}$) von 1.5–2 had been reached.

Main Culture:

For expression, 20 ml of CMdum liquid medium with 2% raffinose and 1% (v/v) Tergitol NP-40 were supplemented with γ-linoleic acid (γ-18:3) to a final concentration of 0.003% (w/v). The media were inoculated with the precultures to an $OD_{600}$ of 0.05. Expression was induced for 16 hours at an $OD_{600}$ of 0.2, using 2% (w/v) galactose, whereupon the cultures were harvested at an $OD_{600}$ of 0.8–1.2.

Fatty Acid Analysis

The overall fatty acids were extracted from yeast cultures and analyzed by means of gas chromatography. To this end, cells of 5 ml culture were harvested by centrifugation (1000×g, 10 minutes, 4° C.) and washed once with 100 mM $NaHCO_3$, pH 8.0, to remove residual medium and fatty acids. To prepare the fatty acid methyl esters (FAMEs), the cell sediments were treated for 1 hour at 80° C. with 1 M methanolic $H_2SO_4$ and 2% (v/v) dimethoxypropane. The FAMEs were extracted twice with 2 ml of petroleum ether, washed once with 100 mM $NaHCO_3$, pH 8.0, and once with distilled water, and dried with $Na_2SO_4$. The organic solvent was evaporated under a stream of argon, and the FAMEs were dissolved in 50 ∝l petroleum ether. The samples were separated on a ZEBRON ZB Wax capillary column (30 m, 0.32 mm, 0.25 αm; Phenomenex) in a Hewlett Packard 6850 gas chromatograph equipped with a flame ionization detector. The oven temperature was programmed from 70° C. (hold for 1 minute) to 200° C. at a rate of 20° C./minute, then to 250° C. (hold for 5 minutes) at a rate of 5° C./minute and finally to 260° C. at a rate of 5° C./minute. Nitrogen was used as the carrier gas (4.5 ml/minute at 70° C.). The fatty acids were identified by comparison with retention times of FAME standards (SIGMA).

Expression Analysis

The fatty acid patterns of five transgenic yeast strains are shown in Table 1 in mol %.

The ratios of the γ-linolenic acid which had been added and taken up are emphasized by numbers printed in bold, those of the elongated products by numbers in red and those of the elongated γ-linolenic acid by numbers printed in bold (last line).

The GC analysis of FAMEs which from total lipids of the yeasts transformed with pYES2 (i/control) and pY2PSE1 is shown in FIG. 1. For the analysis, the transgenic yeasts were cultured in the presence of γ-18:3.

The results demonstrate that γ-18:3 has been incorporated into all transgenic yeasts in large amounts. All four transgenic yeast clones which had been transformed with pY2PSE1 exhibit an additional peak in the gas chromatogram, which was identified as $20:3^{\Delta 8,11,14}$ by a comparison of the retention times. A gas chromatography/mass spectroscopy can provide additional proof to confirm this identity.

The products identified demonstrated that the nucleotide sequence of PiPSE1 encodes a $\Delta^6$-selective fatty acid elongase from the moss Physcomitrella patens, which leads to the formation of novel fatty acids in transgenic yeasts.

Further feeding experiments with a wide range of other fatty acids (for example linoleic acid ($18:2^{\Delta 9,12?}$), stearidonic acid ($18:4^{\Delta 6,9,12,15}$)) can be carried out for confirming the substrate selectivity of this elongase in greater detail.

Example 14

Isolation of the Desired Product From Transformed Organisms in General

The desired product can be obtained from plant material or fungi, algae, ciliates, animal cells or from the supernatant of the above-described cultures by various methods known in the art. If the desired product is not secreted from the cells, the cells can be harvested from the culture by slow centrifugation, and the cells can be lyzed by standard techniques, such as mechanical force or sonication. Plant organs can be separated mechanically from other tissue or other organs. After homogenization, the cell debris is removed by centrifugation, and the supernatant fraction, which contains the soluble proteins, is retained for further isolating the desired compound. If the product is secreted from desired cells, the cells are removed from the culture by slow centrifugation, and the supernatant fraction is retained for the further isolation.

The supernatant fraction from each isolation step is subjected to a chromatography with a suitable resin, the desired molecule either being retained on the chromatography resin while many contaminants in the sample are not, or the contaminants remaining on the resin while the sample does not. These chromatography steps can be repeated, if desired, using either the same or other chromatography resins. The skilled worker is familiar with selecting suitable chromatography resins and with their most effective use for a particular molecule to be isolated. The product isolated can be concentrated by filtration or ultrafiltration and stored at a temperature at which the stability of the product is highest.

A broad spectrum of isolation methods is known in the art, and the isolation method above is not intended to be limiting. These isolation methods are described, for example, in Bailey, J. E., & Ollis, D. F., Biochemical Engineering Fundamentals, McGraw-Hill: New York (1986).

Identity and purity of the compounds isolated can be determined by standard techniques of the art. They include high-performance liquid chromatography (HPLC), spectroscopic methods, staining methods, thin-layer chromatography, NIRS, enzyme assays or microbiological methods. For a review of these analytical methods, see: Patek et al. (1994)

Appl. Environ. Microbiol. 60:133–140; Malakhova et al. (1996) Biotekhnologiya 11:27–32; and Schmidt et al. (1998) Bioprocess Engineer. 19:67–70. Ulmann's Encyclopedia of Industrial Chemistry (1996) Vol. A27, VCH Weinheim, pp. 89–90, pp. 521–540, pp. 540–547, pp. 559–566, 575–581 and pp. 581–587; Michal, G (1999) Biochemical Pathways: An Atlas of Biochemistry and Molecular Biology, John Wiley and Sons; Fallon, A., et al. (1987) Applications of HPLC in Biochemistry in: Laboratory Techniques in Biochemistry and Molecular Biology, Vol. 17.

EQUIVALENTS

The skilled worker knows, or can identify, a number of equivalents of the specific embodiments according to the invention which have been described herein by simply resorting to routine experiments. These equivalents are intended to be covered by the patent claims.

We claim:

1. An isolated nucleic acid encoding a polypeptide that elongates $C_{16}$- or $C_{18}$-fatty acids with at least two double bonds in the fatty acid by at least two carbon atoms, wherein $C_{18:3}^{\Delta 5t,9,12}$, $C_{20:3}^{\Delta 8,11,14}$, $C_{20:4}^{\Delta 5,8,11,14}$ and $C_{20:5}^{\Delta 5,8,11,14,17}$ are not elongated and wherein said nucleotide sequence is selected from the group consisting of:
   a) the sequence of SEQ ID NO:1;
   b) a nucleic acid sequence which, in accordance with degeneracy of the genetic code, is derived from the amino acid sequence of SEQ ID:2; and
   c) derivatives of the sequence of SEQ ID NO:1 which encode polypeptides with at least 95% homology with the amino acid sequence of SEQ ID NO:2, wherein the sequence acts as a $C_{16}$- or $C_{18}$-elongase.

2. The nucleic acid sequence of claim 1, wherein the sequence is derived from an Oomycete.

3. The nucleic acid sequence of claim 1, wherein the sequence is derived from *Phytophthora*.

4. A gene construct comprising the nucleic acid of claim 1, wherein the nucleic acid is functionally linked to one or more regulatory signals.

5. The gene construct of claim 4, wherein the one or more regulatory signals enhance gene expression.

6. A vector comprising the gene construct of claim 4.

7. An isolated host cell comprising a recombinant nucleic acid that encodes a polypeptide, which elongates $C_{16}$- or $C_{18}$-fatty acids with at least two double bonds in the fatty acid by at least two carbon atoms, wherein one or more of $C_{18:3}^{\Delta 5t,9,12}$, $C_{20:3}^{\Delta 8,11,14}$, $C_{20:4}^{\Delta 5,8,11,14}$ and $C_{20:5}^{\Delta 5,8,14,17}$ are not elongated and wherein said nucleotide sequence is selected from the group consisting of:
   a) the sequence of SEQ ID NO:1;
   b) a nucleic acid sequence which, in accordance with degeneracy of the genetic code, is derived from the amino acid sequence of SEQ ID:2; and
   c) derivatives of the sequence of SEQ ID NO:1 which encode polypeptides with at least 95% homology with the amino acid sequence of SEQ ID NO:2, wherein the sequence acts as a $C_{16}$- or $C_{18}$-elongase.

8. The isolated host cell of claim 7, wherein the host cell is a microorganism, a nonhuman animal or a plant cell.

9. The isolated host cell of claim 7, wherein the host cell is a transgenic plant cell.

10. The nucleic acid of claim 1, which encodes a polypeptide that elongates $C_{16}$- or $C_{18}$-fatty acids with at least three double bonds in the fatty acid.

11. The nucleic acid of claim 1, which encodes a polypeptide that elongates $C_{16}$- or $C_{18}$-fatty acids with at least four double bonds in the fatty acid.

12. The nucleic acid of claim 1, wherein the polypeptide shows a preference for elongating $C_{18:3}^{\Delta 6,9,12}$, $C_{18:4}^{\Delta 6,9,12,15}$, or $C_{16:3}^{\Delta 7,10,13}$-fatty acids as compared to one or more of $C_{18:2}^{\Delta 9,12}$, $C_{18:3}^{\Delta 4,7,10}$, $C_{18:3}^{\Delta 5,8,11}$, $C_{18:3}^{7,10,13}$, $C_{18:3}^{\Delta 8,11,14}$, $C_{18:3}^{\Delta 9,12,15}$ or $C_{18:3}^{\Delta 5,c9,12}$-fatty acids.

13. The nucleic acid of claim 12, wherein the preference is at least a factor of 1.5.

* * * * *

UNITED STATES PATENT AND TRADEMARK OFFICE
CERTIFICATE OF CORRECTION

| | |
|---|---|
| PATENT NO. | : 7,179,647 B2 |
| APPLICATION NO. | : 10/502083 |
| DATED | : February 20, 2007 |
| INVENTOR(S) | : Jens Lerchl et al. |

It is certified that error appears in the above-identified patent and that said Letters Patent is hereby corrected as shown below:

On the Title Page: item [54]

Title page, item [57] line 14, in the abstract "acids with at least two double bonds and/or a triacyiglycerol" should read -- acids with at least two double bonds and/or a triacylglycerol--.

In Claim 1, in column 59, on line 26, "amino acid sequence of SEQ ID:2; and" should read -- amino acid sequence of SEQ ID NO:2; and--.

In Claim 7, in column 59, on line 45, "$C_{18:3}^{\Delta 5t,9,12}$, $C_{20:3}^{\Delta 8,11,14}$, $C_{20:4}^{\Delta 5,8,11,14}$, and $C_{20:5}^{\Delta 5,8,14,17}$" should read -- $C_{18:3}^{\Delta 5t,9,12}$, $C_{20:3}^{\Delta 8,11,14}$, $C_{20:4}^{\Delta 5,8,11,14}$ and $C_{20:5}^{\Delta 5,8,11,14,17}$--.

In Claim 7, in column 60, on line 22, "amino acid sequence of SEQ ID:2; and" should read -- amino acid sequence of SEQ ID NO:2; and--.

In claim 8, in column 60, on line 28, "is a microorganism, a nonhuman animal or a plant cell" should read -- is a microorganism, a nonhuman cell or a plant cell--.

UNITED STATES PATENT AND TRADEMARK OFFICE
CERTIFICATE OF CORRECTION

PATENT NO. : 7,179,647 B2
APPLICATION NO. : 10/502083
DATED : February 20, 2007
INVENTOR(S) : Jens Lerchl et al.

It is certified that error appears in the above-identified patent and that said Letters Patent is hereby corrected as shown below:

In Claim 12, in column 60, on line 40, "or more of $C_{18:2}^{\Delta 9,12}$, $C_{18:3}^{\Delta 4,7,10}$, $C_{18:3}^{\Delta 5,8,11}$, $C_{18:3}^{7,10,13}$" should read -- or more of $C_{18:2}^{\Delta 9,12}$, $C_{18:3}^{\Delta 4,7,10}$, $C_{18:3}^{\Delta 5,8,11}$, $C_{18:3}^{\Delta 7,10,13}$ --.

Signed and Sealed this

Eighth Day of May, 2007

JON W. DUDAS
*Director of the United States Patent and Trademark Office*

SEQUENCE LISTING

```
<160> NUMBER OF SEQ ID NOS: 2

<210> SEQ ID NO 1
<211> LENGTH: 1066
<212> TYPE: DNA
<213> ORGANISM: Phytophthora infestans
<220> FEATURE:
<221> NAME/KEY: CDS
<222> LOCATION: (52)..(888)

<400> SEQUENCE: 1
gaattcggca cgaggttcgc acgtccatcg tctactcacc aacaagaagt c atg tcg         57
                                                        Met Ser
                                                          1 act gag cta ctg cag agc tac tac gcg tgg gcc aac gcc acg gag gcc        105
Thr Glu Leu Leu Gln Ser Tyr Tyr Ala Trp Ala Asn Ala Thr Glu Ala
        5                  10                  15 aag ctg ctg gac tgg gtc gac cct gag ggc ggc tgg aag gtg cat cct        153
Lys Leu Leu Asp Trp Val Asp Pro Glu Gly Gly Trp Lys Val His Pro
 20                  25                  30 atg gca gac tac ccc cta gcc aac ttc tcc agc gtc tac gcc atc tgc        201
Met Ala Asp Tyr Pro Leu Ala Asn Phe Ser Ser Val Tyr Ala Ile Cys
 35                  40                  45                  50 gtc gga tac ttg ctc ttc gta atc ttc ggc acg gcc ctg atg aaa atg        249
Val Gly Tyr Leu Leu Phe Val Ile Phe Gly Thr Ala Leu Met Lys Met
                 55                  60                  65 gga gtc ccc gcc atc aag acc agt cca tta cag ttt gtg tac aac ccc        297
Gly Val Pro Ala Ile Lys Thr Ser Pro Leu Gln Phe Val Tyr Asn Pro
         70                  75                  80 atc caa gtc att gcc tgc tct tat atg tgc gtg gag gcc gcc atc cag        345
Ile Gln Val Ile Ala Cys Ser Tyr Met Cys Val Glu Ala Ala Ile Gln
         85                  90                  95 gcc tac cgc aac ggc tac acc gcc gcc ccg tgc aac gcc ttt aag tcc        393
Ala Tyr Arg Asn Gly Tyr Thr Ala Ala Pro Cys Asn Ala Phe Lys Ser
100                 105                 110 gac gac ccc gtc atg ggc aac gtt ctg tac ctc ttc tat ctc tcc aag        441
Asp Asp Pro Val Met Gly Asn Val Leu Tyr Leu Phe Tyr Leu Ser Lys
115                 120                 125                 130 atg ctc gac ctg tgc gac aca gtc ttc att atc cta gga aag aag tgg        489
Met Leu Asp Leu Cys Asp Thr Val Phe Ile Ile Leu Gly Lys Lys Trp
                135                 140                 145 aaa cag ctt tcc atc ttg cac gtg tac cac cac ctt acc gtg ctt ttc        537
Lys Gln Leu Ser Ile Leu His Val Tyr His His Leu Thr Val Leu Phe
        150                 155                 160 gtc tac tat gtg acg ttc cgc gcc gct cag gac ggg gac tca tat gct        585
Val Tyr Tyr Val Thr Phe Arg Ala Ala Gln Asp Gly Asp Ser Tyr Ala
        165                 170                 175 acc atc gtg ctc aac ggc ttc gtg cac acc atc atg tac act tac tac        633
Thr Ile Val Leu Asn Gly Phe Val His Thr Ile Met Tyr Thr Tyr Tyr
180                 185                 190
```

-continued

```
ttc gtc agc gcc cac acg cgc aac att tgg tgg aag aag tac ctc acg      681
Phe Val Ser Ala His Thr Arg Asn Ile Trp Trp Lys Lys Tyr Leu Thr
195                 200                 205                 210 cgc att cag ctt atc cag ttc gtg acc atg aac gtg cag ggc tac ctg      729
Arg Ile Gln Leu Ile Gln Phe Val Thr Met Asn Val Gln Gly Tyr Leu
                215                 220                 225 acc tac tct cga cag tgc cca ggc atg cct cct aag gtg ccg ctc atg      777
Thr Tyr Ser Arg Gln Cys Pro Gly Met Pro Pro Lys Val Pro Leu Met
            230                 235                 240 tac ctt gtg tac gtg cag tca ctc ttc tgg ctc ttc atg aat ttc tac      825
Tyr Leu Val Tyr Val Gln Ser Leu Phe Trp Leu Phe Met Asn Phe Tyr
        245                 250                 255 att cgc gcg tac gtg ttc ggc ccc aag aaa ccg gcc gtg gag gaa tcg      873
Ile Arg Ala Tyr Val Phe Gly Pro Lys Lys Pro Ala Val Glu Glu Ser
    260                 265                 270 aag aag aag ttg taa cggcgcttgt taaaaagtct aacctcgctg taacagctta      928
Lys Lys Lys Leu
275 aaacacacac acacacaacg ctttgtagag gaggtaagta gtggcaactc gtgtagaaat    988 gcagcatgcc catcaaatac atcccgtatg attcaaaaaa aaaaaaaaaa aaaaaaaaaa   1048 aaaaaaaaaa aactcgag                                                 1066

<210> SEQ ID NO 2
<211> LENGTH: 278
<212> TYPE: PRT
<213> ORGANISM: Phytophthora infestans

<400> SEQUENCE: 2

Met Ser Thr Glu Leu Leu Gln Ser Tyr Tyr Ala Trp Ala Asn Ala Thr
  1               5                  10                  15

Glu Ala Lys Leu Leu Asp Trp Val Asp Pro Glu Gly Gly Trp Lys Val
            20                  25                  30

His Pro Met Ala Asp Tyr Pro Leu Ala Asn Phe Ser Ser Val Tyr Ala
        35                  40                  45

Ile Cys Val Gly Tyr Leu Leu Phe Val Ile Phe Gly Thr Ala Leu Met
     50                  55                  60

Lys Met Gly Val Pro Ala Ile Lys Thr Ser Pro Leu Gln Phe Val Tyr
 65                  70                  75                  80

Asn Pro Ile Gln Val Ile Ala Cys Ser Tyr Met Cys Val Glu Ala Ala
                85                  90                  95

Ile Gln Ala Tyr Arg Asn Gly Tyr Thr Ala Ala Pro Cys Asn Ala Phe
            100                 105                 110

Lys Ser Asp Asp Pro Val Met Gly Asn Val Leu Tyr Leu Phe Tyr Leu
        115                 120                 125

Ser Lys Met Leu Asp Leu Cys Asp Thr Val Phe Ile Ile Leu Gly Lys
    130                 135                 140

Lys Trp Lys Gln Leu Ser Ile Leu His Val Tyr His His Leu Thr Val
145                 150                 155                 160

Leu Phe Val Tyr Tyr Val Thr Phe Arg Ala Ala Gln Asp Gly Asp Ser
                165                 170                 175

Tyr Ala Thr Ile Val Leu Asn Gly Phe Val His Thr Ile Met Tyr Thr
            180                 185                 190

Tyr Tyr Phe Val Ser Ala His Thr Arg Asn Ile Trp Trp Lys Lys Tyr
        195                 200                 205

Leu Thr Arg Ile Gln Leu Ile Gln Phe Val Thr Met Asn Val Gln Gly
```

-continued

```
            210                 215                 220
Tyr Leu Thr Tyr Ser Arg Gln Cys Pro Gly Met Pro Pro Lys Val Pro
225                 230                 235                 240

Leu Met Tyr Leu Val Tyr Val Gln Ser Leu Phe Trp Leu Phe Met Asn
                245                 250                 255

Phe Tyr Ile Arg Ala Tyr Val Phe Gly Pro Lys Lys Pro Ala Val Glu
            260                 265                 270

Glu Ser Lys Lys Lys Leu
            275
```